(12) United States Patent
Schardl et al.

(10) Patent No.: US 7,183,098 B2
(45) Date of Patent: Feb. 27, 2007

(54) LOLINE ALKALOID GENE CLUSTERS OF THE FUNGAL ENDOPHYTE NEOTYPHODIUM UNCINATUM

(75) Inventors: Christopher L. Schardl, Lexington, KY (US); Heather H. Wilkinson, College Station, TX (US); Martin J. Spiering, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 475 days.

(21) Appl. No.: 10/601,700

(22) Filed: Jun. 24, 2003

(65) Prior Publication Data
US 2004/0139496 A1   Jul. 15, 2004

Related U.S. Application Data

(60) Provisional application No. 60/390,446, filed on Jun. 24, 2002.

(51) Int. Cl.
*C12P 17/14* (2006.01)
*C07H 21/04* (2006.01)
*A63B 69/36* (2006.01)

(52) U.S. Cl. ............... 435/252.3; 435/120; 435/320.1; 435/252.33; 435/252.8; 435/254.11; 536/23.2

(58) Field of Classification Search ............ 435/252.2, 435/252.3, 252.8, 254.11, 252.33, 320.1; 536/23.2
See application file for complete search history.

(56) References Cited

OTHER PUBLICATIONS

M. Arévalo-Rodriguez et al., "Mutations that Cause Threonine Sensitivity Identify Catalytic and Regulatory Regions of the Aspartate Kinase of *Saccharomyces cerevisiae*", Yeast 15, (1999), pp. 1331-1345.
L.P. Bush et al., "Chemistry, occurrence and biological effects of saturated pyrrolizidine alkaloids associated with endophyte-grass interations", Agriculture, Ecosystems and Environment, 44, (1993), pp. 81-102.
N.P. Keller, "Review: Metabolic Pathway Gene Clusters in Filamentous Fungi", Fungal Genetics and Biology, 21, (1997), pp. 17-29.
J.A. Seo, et al., Characterization of Four Clustered and Coregulated Genes Associated with Fumonisin Biosynthesis in *Fusarium verticillioides*, Fungal Genetics and Biology, 34, (2001) pp. 155-165.
P. Tudzynski et al., "Evidence for an ergot alkaloid gene cluster in *Claviceps purpurea*", Mol. Gen. Genet., (1999), 261, pp. 133-141.
A. Leuchtmann et al., "Different Levels of Protective Alkaloids in Grasses with Stroma-Forming and Seed-Transmitted *Epichloë/Neotyphodium* Endophytes", Journal of Chemical Ecology, vol. 26, No. 4, 2000, pp. 1025-1036.
H.H. Wilkinson et al., "Contribution of Fungal Loline Alkaloids to Protection from Aphids in a Grass-Endophyte Mutualism", MPMI, vol. 13, No. 10, 2000, pp. 1027-1033.

M.R. Siegel et al., "Fungal Endophyte-Infected Grasses: Alkaloid Accumulation and Aphid Response", Journal of Chemical Ecology, vol. 16, No. 12, 1990, pp. 3301-3315.
C.O. Miles et al., "High Levels of Ergonovine and Lysergic Acid Amide in Toxic *Achnatherum inebrians* infection by an Acremonium-like Endophytic Fungus", J. Agric Food Chem., 1996, 44, pp. 1285-1290.
M.R. Tepaske et al., "Analyses of Selected Endophyte-Infected Grasses for the Presence of Loline-Type and Ergot-Type Alkaloids", J. Agric. Food Chem., 1993, 41, pp. 2299-2303.
K.D. Craven et al., "Hybrid fungal endophytes symbiotic with the grass *Lolium pratense*", Sydowia, 53(1), pp. 44-73.
M.J. Christensen et al., Taxonomy of *Acremonium* endophytes of tall fescue (*Festuca arundinacea*), meadow fescue (*F. pratensis*) and perennial rye-grass (*Lolium perenne*), Mycol. Res., 97, (9), (1993), pp. 1053-1092.
A. Leuchtmann et al., "Mating compatibility and phylogenetic relationships among two new species of *Epichloe* and other congeneric European species", Mycol. Res. 12, (10), (1998), pp. 1169-1182.
M.J. Spiering et al., "Expressed sequence tags and genes associated with loline alkaloid expression by the fungal endophyte *Neotyphodium uncinatum*", Fungal Genetics and Biology, (2000), pp. 1-13.
Z Lin et al.,"Rapid Mini-Scale Plasmid Isolation for DNA Sequencing and Restriction Mapping", BioTechniques, vol. 29, Sep. 2000, pp. 466-468.
T.H. Al-Samarrai et al., "A simple method for extraction of fungal genomic DNA", Letters in Applied Microbiology, 2000, vol. 30, pp. 53-56.
S.F. Altschul et al., "Gapped BLAST and PSI-BLAST: a new generation of protein database search programs", Nucleic Acids Research, 1997, vol. 25, No. 17, pp. 3389-3402.
J.D. Blankenship et al., "Production of loline alkaloids by the grass endophyte, *Neotyphodium uncinatum*, in defined media", Photochemistry, Vvol. 58, (2001), pp. 395-401.

(Continued)

*Primary Examiner*—Rebecca E. Prouty
*Assistant Examiner*—Kagnew Gebreyesus
(74) *Attorney, Agent, or Firm*—McDermott Will & Emery LLP

(57) ABSTRACT

Loline alkaloids (LA), which are 1-aminopyrrolizidines with an oxygen bridge, are produced by *Epichloë* (anamorph=*Neotyphodium*) species, endophytes of grasses. LA are insecticidal, thus helping protect host plants from insect herbivory. Suppression subtractive hybridization PCR was used to isolate transcripts up-regulated during loline alkaloid production in cultures of *Neotyphodium uncinatum*. Subtracted cDNAs were cloned, and a λ-phage cDNA library from an LA-expressing *N. uncinatum* culture was screened with subtracted cDNA. In BLAST searches, several cDNAs identified had sequence similarities to aspartate kinases, and another with O-acetylhomoserine-(thiol)lyase. Differential expression of these two genes in LA-producing cultures of *N. uncinatum* was confirmed, and in a survey of 23 isolates from 21 *Neotyphodium* and *Epichloë* species these two genes strictly correlated with LA production. Two nucleic acid molecules encoding two loline alkaloid gene clusters have been identified.

7 Claims, 6 Drawing Sheets

OTHER PUBLICATIONS

M.L. Bogush et al. "Identification and localization of difference between *Escherichia coli* and *Salmonella typhimurium* genomes by suppressive subtractive hybridization", Molecular and General Genetics, (1999), vol. 262, pp. 721-729.

L.P. Bush et al., "Bioprotective Alkalids of Grass-Fungal Endophyte Symbioses[1]", Plant Physiol., (1997), vol. 114, pp. 1-7.

A.D. Byrd et al., "The β-tubulin gene of *Epichloë typhina* from perennial ryegrass (*Lolium perenne*) ", Current Genetics, (1990), vol. 18, pp. 347-354.

L. Diatchenko et al., "Suppression subtractive hybridization: A method for generating differentially regulated or tissue-specific cDNA probes and libraries", Proceedings of the National Academy of Sciences of the United States of America, Jun. 11, 1996, vol. 93, No. 12, pp. 6025-6030.

L. Diatchenko et al., "Suppression Subtractive Hybridization: A Versatile Method for Identifying Differentially Expressed Genes", cDNA Preparation and Characterization, Methods in Enzymology, vol. 303, pp. 349-380.

Y. Wang et al., "A Rapid CTAB DNA Isolation Technique for RAPD Fingerprinting and Other PCR Applications", BioFeedback, vol. 14, No. 5, (1993).

W.O. Endege et al., "Representative cDNA Libraries and Their Utility in Gene Expression Profiling", BioTechniques, vol. 26, No. 2, (Mar. 1999), pp. 542-550.

F.S. Gimble et al., MiniReview, "Invasion of a multitude of genetic niches by mobile endonuclease genes", FEMS Microbiology Letters, vol. 185, (2000), pp. 99-107.

P. Liang et al., "Differential Display of Eukaryotic Messenger RNA by Means of the Polymerase Chain Reaction", Science, vol. 257, Aug. 14, 1992, pp. 987-971.

G. Nicolas et al., "Lack of hepcidin gene expression and severe tissue iron overload in upstream stimulatory factor 2 (*USF2*) knockout mice", PNAS, vol. 98, No. 15, Jul. 17, 2001, pp. 8780-8785.

J. Oscarrsson et al., "Pulsatile growth hormone secretion decreases S-adenosylmethionine synthetase in rat liver" Am. J. Physiol. Endocrinol Metab., vol. 280, pp. E280-E286, 2001.

A. Paszewski et al, "Sulphur Metabolism", Aspergillus: 50 years on, vol. 29, pp. 299-319.

R.H. Proctor et al., "*Tri6* Encodes an Unusual Zinc Finger Protein Involved in Regulation of Trichothecene Biosyntheses in *Fusarium sporotrichioides*", Applied and Environmental Microbiology, vol. 61, No. 5, May 1995, pp. 1923-1930.

D.V. Rebrikov et al., "Mirror orientation selection (MOS): a method for eliminating false positive clones form libraries generated by suppression subtractive hybridization", Nucleic Acids Research, 2000, vol. 28, No. 20, e90, pp. 1-4.

C.L. Schardl et al., "Review: *Epichloë festucae* and Related Mutualistic Symbionts of Grasses", Fungal Genetics and Biology, vol. 33, pp. 69-82, (2001).

M. Sienko et al., "Structure and reguation of *cysD*, the homocysteine synthase gene of *Aspergillus nidulans*", Current Genetics, (1998), vol. 33, pp. 136-144.

B. Tofern et al., Occurrence of loline alkaloids in *Argyreia mollis* (Convolvulaceae), Phytochemistry, vol. 51, (1999), pp. 1177-1180.

T. Yasuta et al., "DNA Sequence and Mutational Analysis of Rhizobitoxine Biosysnthesis Genes in *Bradyrhizobium elkanii*" Applied and Environmental Microbiology, vol. 67, No. 11, Nov. 2001, pp. 4999-5009.

B. Zhumabayeva et al., "Use of SMART™- Generated cDNA for Gene Expression Studies in Multiple Human Tumors", BioTechniques, vol. 30, No. 1, Jan. 2001, pp. 158-163.

| | R | R' |
|---|---|---|
| Loline | CH₃ | H |
| Norloline | H | H |
| N-Methylloline | CH₃ | CH₃ |
| N-Formylloline | CH₃ | CHO |
| N-Formylnorloline | H | CHO |
| N-Acetylloline | CH₃ | COCH₃ |
| N-Acetylnorloline | H | COCH₃ |

Fig. XX. *Loline* alkaloid biosynthesis genes

LOLINE ALKALOID GENE CLUSTERS OF THE FUNGAL ENDOPHYTE NEOTYPHODIUM UNCINATUM

RELATED APPLICATIONS

The present application claims the benefit of the priority date of provisional patent application No. 60/390,446, filed Jun. 24, 2002. The complete disclosure of the earlier filed application is incorporated by reference herein.

GOVERNMENT SUPPORT

The present invention was supported by the United States National Science Foundation Integrative Plant Biology Program 9808554 to C.L.S. and the United States Department of Agriculture NRICGP grant 9901343.

FIELD OF THE INVENTION

The present invention relates generally to alkaloids and alkaloid biosynthesis. In particular, the invention pertains to the nucleic acids encoding loline alkaloid synthesis genes and the tailoring enzymes of loline alkaloid biosynthesis, and to recombinant vectors and host cells containing such genes, and to the recombinant production of alkaloids and uses thereof.

BACKGROUND OF THE INVENTION

Loline alkaloids (LA; saturated 1-aminopyrrolizidine alkaloids with an ether bridge, FIG. 1), are produced in a number of associations of grasses with endophytes of the genus *Epichloë* and their asexual descendants, *Neotyphodium* spp. In addition, LA are reported from the plants *Adenocarpus* spp. and *Argyreia mollis* of the families Fabaceae and Convolvulaceae, respectively. LA produced in grass-endophyte symbioses have strong insecticidal and feeding-deterrent properties (Riedell,et al., 1999, *J Entomol. Sci.* 26: 122–129; Wilkinson et al., 2000, *Mol. Plant-Microbe Interact.* 13: 1027–1033). Moreover, grasses infected by LA-producing endophytes, such as *Neotyphodium coenophialum* and *N. uncinatum*, have greater tolerance to drought conditions (Arechavaleta et al., 1989, *Agron. J* 81: 83–90; Bacon, 1993, *Agric. Ecos. Environ.* 44: 123–141 ) than grasses infected by closely related endophytes, such as *N. lolii*, that do not produce LA (Barker et al., 1997, *Agric. Ecos. Environ.* 44: 123–141; Cheplick et al., 2000, Mycol. Res. 97: 1083–1092.). Growth suppression (allelopathy) of neighboring plants by meadow fescue (*Lolium pratense*) infected with N. *uncinatum* may indicate a potential for additional beneficial roles of these alkaloids in grass plant competitiveness and persistence.

LA can accumulate to extremely high levels in grass tissues, occasionally reaching more than 2% of the plant's dry mass (Craven et al., 2001, *Sydowia* 53: 44–73). These quantities far exceed the biomass of the fungus and the amounts of other alkaloids, such as ergot alkaloids, indole-diterpenoids, and peramine, also produced in some of the endophyte-grass symbiota. However, despite their exceptional levels in the grass and importance of LA in grass survival, little is known about LA biosynthesis. This is in contrast to some of the other endophyte-associated alkaloids, such as ergopeptines and indole-diterpenoids, for which much of the biosynthetic pathways have been elucidated and key enzymes identified.

It was previously unknown whether LA are of fungal or plant origin, or produced by both symbiotic partners together, but a recent study has established that *N. uncinatum* can produce LA in axenic culture (Blankenship et al., 2001, *Phytochemistry* 58: 395–401). This finding presents opportunities to identify genes involved in LA biosynthesis. Knowledge of the LA biosynthesis genes would allow more detailed studies on the roles of LA in plant persistence, in particular on possible contributions to abiotic stress tolerance, as well as the cloning and use of these genes to generate genetically engineered plants.

SUMMARY OF THE INVENTION

In one aspect, the present invention provides isolated nucleic acid compounds comprising at least a sequence identical or complementary to all or part of a coding sequence for the loline alkaloid biosynthetic gene cluster from *Neotyphodium uncinatum* (SEQ ID NO. 15, and SEQ ID NO. 16). It appears that SEQ ID NO: 17 may be linked to the 5' end of SEQ ID NO: 16. Preferably, a part of said coding sequence is an open reading frame (ORF) selected from the group consisting of ORF1, ORF2, ORF3, ORF4, ORF5, ORF6, ORF7, ORF8, ORF9, ORF1', ORF2', ORF3', ORF4', ORF5', ORF6', ORF7', ORF8', ORF9' or ORF10'. More preferably, a part of said coding sequence is an ORF selected from the group consisting of ORF1, ORF2, ORF3, ORF4, ORF5, ORF6, ORF7, ORF8, ORF9, ORF1', ORF2', ORF3', ORF4', ORF5', ORF6', ORF7', and ORF8'.

In one embodiment, the present invention provides an isolated nucleic acid strand that encodes a loline alkaloid gene cluster or subunit thereof comprising a nucleotide sequence identical or complementary to, or an amino acid sequence encoded by a nucleotide sequence identical or complementary to, all or part of a coding sequence for loline alkaloid biosynthetic gene cluster of SEQ ID NO. 15 or SEQ ID NO. 16. Preferably, the gene cluster encodes a functional gene cluster and optionally, selected tailoring enzymes. The gene cluster may be derived from a single species or may be hybrid in nature. In certain embodiments, the gene cluster is a replacement gene cluster. The replacement gene cluster may be a variant, hybrid, mutant, analog or derivative thereof.

In another embodiment, the invention provides an isolated nucleic acid that encodes three or more ORFs comprising a sequence identical or complementary to all or part of a coding sequence for enzymes performing the biosynthesis of loline alkaloids from *Neotyphodium uncinatum*. Preferably, the ORFs encode a functional gene cluster and optionally, selected tailoring enzymes. In certain embodiments, an ORF may be derived from a single species or may be hybrid in nature. In certain embodiments at least one of the ORFs is native to the loline alkaloid gene cluster of SEQ ID NO. 15 or SEQ ID NO. 16. In certain other embodiments, at least one of the ORFs is native to SEQ ID NO: 17. In still other embodiments, at least one ORF is derived from a non-loline alkaloid producing *Neotyphodium* strain, or is hybrid in nature. In yet other embodiments, at least one ORF is a variant, mutant, analog or derivative of the native coding sequence of SEQ ID NO: 15, SEQ ID NO: 16 or SEQ ID NO: 17.

In still another embodiment, the present invention provides isolated nucleic acid compounds comprising three or more genes of the coding sequence for the biosynthesis of loline alkaloids. Preferably, the mixture of genes encode a functional gene cluster and optionally, selected tailoring enzymes. In certain embodiments, a gene may be derived from a single species or may be hybrid in nature. In certain embodiments at least one gene is derived from a loline alkaloid biosynthetic gene cluster. In other embodiments, at least one gene is derived from a non-loline alkaloid producing *Neotyphodium* strain, or is hybrid in nature. Non-limiting exemplary non-*Neotyphodium* biosynthetic genes are preferably subunits of the *Neotyphodium australiense*, *Neotyphodium huerfanum*, *Neotyphodium inebrians*, *Neotyphodium lolii*, and *Neotyphodium melicicola* gene clusters. In yet other embodiments, at least one gene may be a variant, mutant, analog or derivative of the native coding sequence of SEQ ID NO: 15, SEQ ID NO: 16 or SEQ ID NO: 17. It is also preferred that the encoded activity of the gene is that of, for example and without limitation, an epoxidase, α-type pyridoxal phosphate (PLP) associated enzymes, including, by example, class-v aminotransferase, cytochromes P450, aspartate kinase allosteric amino acid binding domain, oxidoreductase, ornithine decarboxylase, γ-type PLP enzyme, FAD-containing monooxygenase, and cyclohexanone oxidase.

In another aspect, the present invention provides recombinant expression vectors encoding a loline alkaloid gene cluster, or variants, hybrids, mutants, analogs or derivatives thereof. In embodiments, vectors encode one or more subunit of a loline alkaloid gene cluster, or variants, hybrids, mutants, analogs or derivatives thereof.

In another aspect, the present invention provides a host cell transformed with a recombinant expression vector described herein.

In still another aspect, the invention provides a method of preparing loline alkaloid, said method comprising introducing a recombinant vector that encodes a loline alkaloid gene cluster or subunit thereof into a host cell, culturing said host cell under conditions such that loline alkaloid is produced or expressed, and isolating the loline alkaloid from the host cell. In one embodiment, the method is practiced with an *E. coli* host cell. The gene cluster may be a replacement gene cluster and preferably a functional gene cluster. In certain embodiments, the invention provides methods for preparing new alkaloid-type compounds, preferably, loline-type alkaloids. The loline-type alkaloid produced may be loline alkaloid or loline alkaloid variants, hybrids, mutants, analogs or derivatives thereof. Such alkaloids are useful as an insecticide.

These and other embodiments and aspects of the invention will be more fully understood after consideration of the attached Drawings and their brief description below, together with the detailed description, example, and claims that follow.

DETAILED DESCRIPTION OF THE INVENTION

Figure 1:
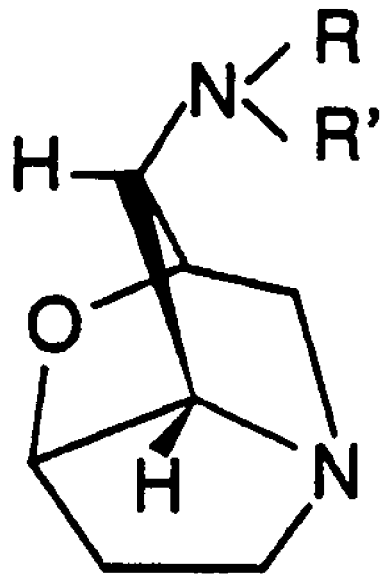
FIG. 1 shows the structures of the loline alkaloids found in certain grass—*Epichloë/Neotyphodium* symbiota. N-Formylloline and N-acetylnorloline were abundant in *N. uncinatum* grown in LA-inducing medium.

Given the valuable agricultural properties of loline alkaloids, there is a need for methods and reagents for producing large quantities of loline-type alkaloids, for producing loline-type alkaloids in host cells that do not produce loline alkaloids naturally, and for producing novel loline-type alkaloids not found in nature. The present invention provides the protein encoding nucleic acids and methods that produce loline-type alkaloids, with particular application to methods for producing the loline alkaloids and variants, hybrids, mutants, analogs, derivatives and novel compounds related through structure or genetics to loline alkaloid.

The practice of the present invention will employ, unless otherwise indicated, conventional methods of chemistry, microbiology, molecular biology and recombinant DNA techniques within the skill of the art. Such techniques are explained fully in the literature. See, e.g., Maniatis, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition).

All publications, patents and patent applications cited herein, whether supra or infra, are hereby incorporated by reference in their entirety.

Definitions

As used herein, the term "alkaloid-type compound" refers to a compound or molecule that is encoded by at least one native alkaloid subunit, or variant, hybrid, mutant, analog, or derivative thereof, including for example, without limitation, loline-type alkaloid.

As used herein, the term "allele" refers to one of two or more alternate forms of a gene occupying the same locus in a particular chromosome or linkage structure and differing from other alleles of the locus at one or more mutational sites. Non-limiting types of alleles include, neutral, amorphs, hypomorphs, hypermorphs, antimorphs, neomorphs, isoalleles and unstable alleles.

As used herein the term "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. A transcription termination sequence will usually be located 3' to the coding sequence.

As used herein the term DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

As used herein the term "functional gene cluster" refers to a set of genes (e.g., three or more) or subunits of a biosynthesis gene cluster, which catalyzes the synthesis of an active or functional alkaloid.

As used herein the term "gene" refers to a segment of DNA or its complement that is involved in producing a polypeptide chain, including regions preceding (leader) and following (trailer) the coding sequence as well as intervening sequences (introns) between individual coding sequence (exons). A "loline alkaloid gene" refers to at least any of the ORFs of SEQ ID NO. 15 and SEQ ID NO. 16.

As used herein the term "gene cluster" refers to a set of (e.g., three or more) closely related genes that code for the same or similar proteins and which are usually grouped together on the same chromosome. A "loline alkaloid gene cluster" refers to a set of genes (e.g., three or more) encoded by at least any of the ORFs of SEQ ID NO. 15 or SEQ ID NO. 16.

As used herein the term "genetically engineered host cell" is meant a host cell where the native gene cluster or subunits thereof has/have been deleted using recombinant DNA techniques. Thus, the term would not encompass mutational events occurring in nature. A "host cell" is a cell derived from a procaryotic microorganism or a eucaryotic cell line cultured as a unicellular entity, which can be, or has been, used as a recipient for recombinant vectors bearing the alkaloid gene clusters of the invention. The term includes the progeny of the original cell which has been transfected. It is understood that the progeny of a single parental cell may not necessarily be completely identical in morphology or in genomic or total DNA complement to the original parent, due to accidental or deliberate mutation. Progeny of the parental cell, which are sufficiently similar to the parent to be characterized by the relevant property, such as the presence of a nucleotide sequence encoding desired biosynthetic enzymes, are included in the definition, and are covered by the above terms.

As used herein the term "loline alkaloid analog" or "analog" refers to a compound or molecule that resembles a loline alkaloid and that contains one or more structural differences relative to the loline alkaloid. Preferably, the loline analog has a desired activity of loline alkaloid although a loline analog may have enhanced or the same activity than products of the loline alkaloid gene cluster. For example, the degree of saturation of at least one bond in the loline alkaloid structure can be changed (e.g., a single bond can be changed to a double or triple bond, or the converse), a bond can be removed, one or more carbon, oxygen or hydrogen atoms can be replaced with a different atom or a chemical moiety (e.g., a halogen, oxygen, nitrogen, sulfur, hydroxy, methoxy, alkyl, aryl, cycloalkyl, heterocycle, amine, amide, ketone, aldehyde, etc.) and the like. Also other peripheral groups, such as OH groups, methyl groups, O-methyl groups, halogene atoms etc. can be added, modified or removed. Other types of derivatives of loline that would be encompassed by the term "loline alkaloid analog" are known in the art. Non-limiting examples are norloline, N-methylloline, N-formylloline, N-formylnorloline, N-acetylloline and N-acetylnorloline.

As used herein the term "loline alkaloid derivative" or "derivative" refers to a compound or molecule, that may be produced from loline in one or more steps or with few chemical or moiety modifications.

As used herein the term "loline-type alkaloid" refers to a compound or molecule that is encoded by one or more native gene of, or a variant, hybrid, mutant, analog or derivative thereof, at least SEQ ID NO. 15 or SEQ ID NO. 16.

As used herein, the term "modification enzyme" or "tailoring enzyme" refers to a protein or enzyme that is involved in modifying an alkaloid after its core has been synthesized by the necessary components to catalyze the production of an active or functional alkaloid. Exemplary, modification enzymes involved in loline-type alkaloid synthesis include, without limitation, oxidoreductases, dioxygenases and N-methyltransferase.

As used herein, the term "modification step" or "tailoring step" refers to an action or actions taken by a protein or enzyme to modify an alkaloid after its core has been synthesized by the necessary components to catalyze the production of an active or functional alkaloid.

As used herein the term "mutant" refers to a nucleic acid compound, protein, molecule, vector or cell resulting from mutation of the native wild type coding sequence or subunits thereof.

As used herein the term "mutation" refers to any change that alters a native coding sequence either by displacement, addition, deletion, insertion, cross-linking, or other destruction or substitution of one or more nucleotides of the native coding sequence. Techniques for modifying nucleotide sequences, such as site-directed mutagenesis, are also known to those skilled in the art.

As used herein the term "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences, and complements thereof. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A transcription termination sequence will usually be located 3' to the coding sequence.

As used here the term "open reading frame" or "ORF" refers to a region of a nucleic acid molecule that contains a series of triplet bases coding for amino acids without any termination codons. An "open reading frame" includes any start codons.

As used herein the term "replacement gene cluster" is meant any set of genes (e.g., three or more), optionally including genes encoding modification or tailoring enzymes, capable of producing a functional gene cluster when under the direction of one or more compatible control elements, as defined above, in a host cell transformed therewith. The term "replacement gene cluster" encompasses three or more genes encoding for the various proteins necessary to catalyze the production of an alkaloid. A "replacement gene cluster" need not include all of the genes found in the corresponding cluster in nature. Rather, the gene cluster need only encode, but is not limited to, the necessary components to catalyze the production of an active alkaloid. For example, if the gene cluster includes, for example, eight genes in its native state and only three of these genes are necessary to provide an active alkaloid, only these three genes need be present, and a variety of the non-necessary genes may optionally be present. The term, "replacement gene cluster" may also contain genes coding for modification or tailoring enzymes or tailoring enzymes to the core alkaloid catalyzed by the necessary components to catalyze the production of an active or functional alkaloid. Furthermore, a replacement gene cluster can include genes derived from a single species, or may be hybrid in nature with, e.g., a gene derived from a cluster for the synthesis of a particular alkaloid replaced with a corresponding gene from a cluster for the synthesis of another alkaloid. Hybrid clusters can include genes derived from different species. The genes included in the replacement gene cluster need not be the native genes, but can be variants, mutants or analogs thereof. Variants are prepared by methods known in the art (see Maniatis et al. Molecular Cloning: A Laboratory Manual (Current Edition)). Mutants or analogs may be prepared by the deletion, insertion or substitution of one or more nucleotides of the coding sequence. Techniques for modifying nucleotide sequences, such as site-directed mutagenesis, are described in the literature. The genes included in the replacement gene cluster need not be on the same plasmid or if present on the same plasmid, can be controlled by the same or different control sequences.

As used herein, the term "subunit" refers to a part of a gene cluster including, for example, a module, domain, gene, or open reading frame, and parts thereof. A "subunit" may comprise for example, a gene or genes derived from a single species or may be hybrid in nature (e.g., a gene derived from a cluster for the synthesis of a particular alkaloid replaced with a corresponding gene from a cluster for the synthesis of another alkaloid.). A "subunit" may comprise variants, mutants, analogs or derivatives of the native gene(s). Variants, mutants, analogs or derivatives thereof may be prepared by techniques known to those of skill in the art, including, without limitation, the displacement, addition, deletion, insertion, cross-linking, or other destruction or substitution of one or more nucleotides of the coding sequence. Techniques for modifying nucleotide sequences, such as site-directed mutagenesis, are also known in to those skilled in the art.

As used herein the term "loline alkaloid variant" or "variant" refers to a nucleic acid sequence that hybridizes to an isolated nucleic acid sequence under high stringency conditions and has a desired or enhanced activity of the complement. Variants may include alleles, mutants, hybrids, derivatives, or analogs. Variants also include the polypeptides coded for by these hybridizable nucleic acids.

Identification of lolA and lolC

Production of LA in *N. uncinatum* can be regulated by culture conditions, such as carbon and nitrogen source and pH in the culture medium, and is completely suppressed in a complex medium (Blankenship et al., 2001, *Phytochemistry* 58: 395–401), suggesting differential expression of genes involved in LA biosynthesis. Isolation of the genes up-regulated during LA production is a first step in identifying possible enzymes in the biosynthesis of the LA. Different methods are now available for the isolation of differentially expressed genes (Diatchenko et al., 1996, *Proc. Natl. Acad. Sci. USA* 93: 6025–6030; Liang and Pardee, 1992, *Science* 257: 967–971), incorporated herein. One such method, suppression subtractive hybridization (Diatchenko et al., 1996; Diatchenko et al., 1999, *Meth. Enzymol.* 303: 349–380) (incorporated herein), has been particularly useful for identifying differentially expressed genes. This technique was used herein to identify genes up-regulated in *N. uncinatum* during LA production.

Culture conditions inducing or suppressing LA alkaloid accumulation in the fungus *N. uncinatum* (Blankenship et al., 2001) were used in combination with suppression subtractive hybridization for isolation of gene transcripts that are up-regulated during LA production. This approach was highly effective in enriching cDNAs differentially expressed in LA-producing cultures: subtracted cDNAs hybridized much more strongly with cDNAs from LA-producing cultures than with cDNAs from LA-suppressed cultures (See FIG. 2). However, a few weak hybridizing bands were present in the total cDNA from the suppressed cultures, which was expected because very low LA levels accumulated in the suppressed cultures. Success of the approach was further indicated by the identification of lolA and lolC, genes that were present only in the species and isolates that produced LA, and, in the case of lolC, related to a sequence previously found to cosegregate with the LA-producing phenotype in Mendelian analysis of *E. festucae* (Wilkinson et al., 2000, *Mol. Plant-Microbe Interact*. 13: 1027–1033). The relationships of lolA and lolC to known biosynthetic enzymes further suggested that this approach identified transcripts of LA biosynthesis genes.

The subtracted cDNAs comprised approximately 6–7% of all transcripts present in LA-producing cultures. This estimation appears reliable, since the number of independent clones in the cDNA library from LA-producing cultures ($4.1\times10^6$ pfu) greatly exceeds the number of clones ($1.0\times10^6$ pfu) estimated to be required for a library representing the complexity of the original mRNA population (Ausubel et al., 2001).

A relatively small number of the subtracted cDNAs and cDNA library clones were sequenced. Rather than conducting extensive sequencing, we focused on some of the cDNAs sequenced in this smaller survey, like lolA and lolC, giving significant similarity to known genes in amino acid biosynthesis/conversion, to further test their association with LA production. These cDNAs appeared promising candidates, since it has been hypothesized earlier that LA have polyamines as precursors, which in turn are products from amino acid metabolism.

Among cDNAs isolated by the subtraction five independent clones from two alleles of genes designated lolA were identified. However, *N. uncinatum* has at least two copies of lolA and lolC. The lolA alleles encode predicted proteins significantly similar to aspartate kinases, the first step in biosynthesis of methionine, threonine, and isoleucine from aspartate. In addition, one cDNA clone of a gene, lolC, with similarity to fungal enzymes in methionine biosynthesis was identified. Expression of lolA and lolC was clearly up-regulated in the LA-producing cultures compared to expression in the suppressed cultures. Further evidence for involvement of lolA and lolC in LA production was the distribution of these genes among the *Neotyphodium* and *Epichloë* species surveyed, of which eight species produce LA, 12 do not, and one (*E. festucae*) is polymorphic for this phenotype. Restriction of lolA and lolC to LA-producing endophytes indicated that both genes are either involved or physically linked to genes involved in the LA production phenotype. This observation, coupled with the observed up-regulation of lolA and lolC in the LA-producing cultures, lent support to an involvement of both genes in LA production.

Generation of knock-outs of lolA and/or lolC will provide further evidence of their roles in LA production. However, preliminary evidence indicates that *N. uncinatum* has at least two alleles of lolA and the possibility of more than one allele of lolC. Thus, different approaches will be necessary to generate complete knock-outs, one of which could be disruption of the putative lol genes in *N. coenophialum* for which procedures for knock-outs and double knock-outs have recently been developed.

The ORFs of the lolA alleles in *N. uncinatum* predicted proteins with lengths of approximately 210 amino acids, much shorter than the sizes of known aspartate kinases (for example, aspartate kinase of *Sc. pombe*, GenBank accession T39822, has a length of 519 amino acids). Potential reasons for this disparity could include truncation in the RT-PCR due to incomplete extension by the reverse transcriptase, or incorrect annealing of the 5' and 3' end-specific cDNA primers to internal gene sequences. cDNA-based northern analysis (see FIG. 3), indicated a strong band of the expected size for an mRNA encoding 210 amino acids, whereas incomplete extension would probably have resulted in multiple bands or smear in the total cDNA. Moreover, despite being very close in size, the two allelic lolA cDNAs varied in the lengths of their 5' and 3' terminal sequences (not shown). Because of this difference, truncation due to incorrect primer annealing also appears unlikely, leaving the possibility that the lolA gene encodes a protein much shorter than known aspartate kinases. The predicted lolA amino acid sequences have similarity only to the C-terminal region of aspartate kinase, but not to the N-terminal regions, containing regions for substrate affinity and the active center (Arévalo-Rodríguez et al., 1999). A search of the PROSITE database further indicated that the predicted lolA sequences do not have an N-terminal consensus sequence typical of aspartate kinases. The C-terminal region of aspartate kinases, to which the predicted lolA products have similarity, is thought to be involved in allosteric response of the enzyme (Arévalo-Rodríguez et al., 1999). It is thus possible that the predicted lolA proteins may have a binding site for an allosteric modulator similar to the modulators acting on aspartate kinase, which are normally allosterically regulated by the amino acids lysine, threonine, or isoleucine.

Multiple steps have been identified for the biosynthesis of the more common plant pyrrolizidines, the senecio alkaloids. Senecio alkaloids are synthesized from polyamines, such as putrescine (derived from decarboxylated ornithine) and spermidine. In part because of their structural similarities with senecio alkaloids, a pathway from polyamines has been proposed for LA (Bush et al., 1993). Relative positions of carbon and nitrogen atoms in the 1-aminopyrrolizidine structure (see FIG. 1) would be consistent with spermidine or a related compound as precursor, and spermidine is ultimately derived from the amino acids ornithine and methionine. Aspartate kinase and homocysteine synthase (or related enzymes) are steps in biosynthesis of methionine, which in turn is a precursor to decarboxylated S-adenosyl-methionine, the source of the aminopropyl moiety of spermidine. The association of lolA and lolC with LA production indeed suggests possible LA-biosynthesis from aspartate via methionine. However, the substantial differences between predicted lolA and known aspartate kinases may cast doubt on this possibility. Nevertheless, we have observed specific incorporation of 4-[$^{13}$C]-Asp into LA, indicating that aspartate is a precursor, although the exact sequence of biosynthetic steps remains to be established. Moreover, lolC also had similarity to an enzyme in the biosynthesis of rhizobitoxine, a bacterial product which enhances nodulation. The activity of this enzyme encompasses formation of serinol and dihydrorhizobitoxine biosynthesis, thus synthesis of compounds different from methionine precursors, further indicating that LA biosynthesis could differ from common amino acid and/or polyamine biosynthesis.

Another cDNA obtained with the subtraction had similarity to a putative zinc-finger transcription factor. Interestingly, in fungi such as *Fusarium sporotrichioides* and *Em. nidulans*, transcriptional regulators can be part of secondary metabolite pathway clusters, raising the possibility that a specific transcriptional regulator also exists for LA genes. The probable transcription factor found here has similarities to C2H2 zinc-finger transcription factors. A C2H2-like transcription factor was found to be involved in the control of genes in the biosynthesis of trichothecene, a secondary metabolite produced by *F. sporotrichioides*. In our study, however, detection of the C2H2-like gene did not correlate with LA production in endophytes. Therefore, it likely that this putative transcription factor might be specifically expressed in *N. uncinatum* under the culture condition used to induce LA production, but may not be a specific regulator for LA biosynthesis genes. Another possibility, however, is that this factor regulates LA genes in *N. uncinatum*, but different factors regulate the orthologous genes in other endophyte species. In fact, loline alkaloids are not produced by other endophyte species in these culture conditions despite the presence of lolA and lolC, and despite their production of LA when symbiotic with plants. Therefore, the possibility of a unique regulator of LA synthesis in *N. uncinatum* warrants further investigation.

Other genes up-regulated during LA production that gave significant matches with known genes or sequences were a putative homing endonuclease, generally associated with unusual DNA splicing and incorporation events, and significant matches of cDNAs to sequences in the *Neurospora crassa* genome. However, for none of these genes do we currently have direct evidence for involvement in LA production. One sequence identified in four clones (P3, K8, C37, D5) was also detectable (by Southern blot) in at least one non-producer, *E. festucae* CBS 102477, but not in the LA producers *N. coenophialum* ATCC 90664 and *E. festucae* CBS 102475 (data not shown), suggesting that this gene is not involved in LA production.

Further Investigations into Biosynthesis of the Loline Alkaloids.

Very little is known about the regulation of secondary metabolism in grass endophytes and many other fungi. The approach used here is a crucial step towards elucidating the biosynthesis of LA, allowing the isolation of genomic copies of *N. uncinatum* genes closely associated with LA production. Secondary metabolite pathway genes are frequently clustered in fungal genomes (Keller and Hohn, 1997, *Fung. Genet. Biol.* 21: 17–29; Seo et al., 2001, *Fung. Genet. Biol.* 34: 155–165; Tudzynski et al., 1999, *Mol. Gen. Genet.* 261: 133–141). The finding of genes associated with LA production now permits investigations of potential clustering of LA genes in genomes of LA-producing endophytes.

EXAMPLE 1

All chemicals (including antibiotics) and reagents used in the experiments described in the examples below were obtained from Sigma Corp. (St. Louis, Mo., USA), unless indicated otherwise. Growth media were from Difco Laboratories (Detroit, Mich., USA). Agarose for DNA and RNA gel electrophoreses was supplied by Bio Whittaker Molecular Applications (Rockland, Me., USA). For routine PCR of templates <1.0 kb, AmpliTaq Gold (Applied Biosystems, Foster City, Calif., USA) was used. PCRs for cDNA synthesis, suppression subtractive hybridization, and templates >1.0 kb were performed with the Advantage cDNA PCR Kit (Clontech, Palo Alto, Calif., USA).

Fungal Cultures and Analyses of Loline Alkaloids.

Mycelium of *Neotyphodium uncinatum* (voucher specimen CBS 102646 at Centraalbureau Voor Schimmelcultures, Utrecht, The Netherlands) was isolated from grass leaf tissues [meadow fescue (*Lolium pratense=Festuca pratensis*), plant 167 in our plant collection] on potato dextrose agar as previously described (Blankenship et al., 2001). The following procedures were carried out as described by Blankenship et al. (2001) with modifications. After 21 days of growth at 22° C. on PDA plates, 10 fungal colonies were transferred to, and homogenized in, 20 ml of LA-inducing medium (Blankenship et al., 2001) with 15 mM asparagine and 20 mM sucrose as the nitrogen and carbon sources, respectively. Ten ml of the homogenate was added to a 500-ml Erlenmeyer flask with 100 ml of fresh LA-inducing medium, and the culture incubated at 22° C. with rotary shaking (100 rpm). After five days of growth, mycelium was harvested in 50-ml tubes (Falcon, distributed by Becton Dickinson Labware, Lincoln Park, N.J., USA) by centrifugation (2000×g rcf), and the mycelium homogenized in 20 ml LA-inducing medium as described. To initiate main cultures for LA production, 1 ml of homogenized mycelium was added to 25 ml of LA-inducing medium and cultures were incubated as described above. To suppress LA production in cultures, but maintain growth conditions similar to the minimal medium, potato dextrose broth was added to give half-strength final concentration in the medium, and asparagine and sucrose were added to 7.5 mM and 10 mM final concentration, respectively. Except for this variation in medium composition, all growth conditions and source of inoculum for LA-suppressed cultures were the same as for LA-induced cultures. Cultures of *N. uncinatum* were grown under the conditions inducing or suppressing LA accumulation, and harvested during early accumulation when LA levels in the producing medium were <20 µg ml$^{-1}$. (Levels in similar cultures later reached >1000 µg ml$^{-1}$ in producing, but <10 µg ml$^{-1}$ in suppressed cultures.)

LA extraction from freeze-dried culture filtrates or plant tissues, and quantitation by gas chromatography (GC) analysis, were performed as described by Blankenship et al. (2001).

RNA Extraction, DNase Treatment, and Analysis.

Mycelium was harvested by vacuum filtration through Whatman No. 1 filter paper (Whatman International Ltd, Maidstone, England, UK) and total RNA was extracted from 0.2–0.3 g (fresh weight) mycelium with the RNeasy Plant Minikit (Qiagen Inc, Valencia, Calif., USA). Co-purified DNA was removed with the DNA-free™ kit (Ambion, Austin, Tex., USA) by treating the extracts (50 µl) with 2 units of DNaseI for 30 min at 37° C., whereupon DNase activity was stopped with DNase Inactivation Reagent (Ambion). Purified RNA was quantified by measuring absorbance at 260 nm and 280 nm in a Genequant spectrophotometer (Amersham Pharmacia Biotech, Piscataway, N.J., USA). Integrity of the total RNA was checked by electrophoresis in 1.2% formaldehyde agarose gels.

cDNA Synthesis and Suppression Subtractive Hybridization.

Total RNA was extracted from LA-producing and LA-suppressed cultures. However, low mycelial biomass resulted in low RNA yields. To obtain enough cDNA for subtractive hybridization and expression analysis (cDNA-based Northems; Endege et al., 1999, *BioTechniques* 26: 542–548), cDNA was synthesized and amplified with the SMART™ PCR cDNA Synthesis Kit (Clontech). Three µl of RNA solution (300 ng/µl) was reverse transcribed with Superscript™ II following the instructions of the manufacturer (Gibco BRL, Grand Island, N.Y., USA). The reverse-transcription reaction was diluted with TE buffer to a total volume of 50 µl. Amplification of cDNA by long-distance PCR was carried out according to the protocol of the SMART™ PCR cDNA Synthesis Kit (Clontech) in a Gene-Amp PCR System 2400 thermocycler (Perkin Elmer Inc., Boston, Mass.). One µl of the diluted reverse-transcription reaction was used, and the number of PCR cycles required for optimum amplification of cDNA was determined according to the manufacturer's protocol (Clontech). The amplification step allows bulking up on cDNA, while likely maintaining the complexity of the original RNA population.

Suppression subtractive hybridization (Diatchenko et al., 1996; Diatchenko et al., 1999) was performed with the PCR-Select™ cDNA Subtraction Kit (Clontech) essentially as described in the Clontech PCR-Select™ manual. The PCR-Select procedure consists of RsaI digestion of cDNA, ligation of digested tester DNA (containing differentially expressed genes of interest) to two adaptors (1 and 2R, specified in the manual), and two rounds of hybridization with driver DNA used to subtract out cDNAs not differentially expressed in the tester, followed by amplification of the subtracted cDNA by PCR with primers specific to the adaptors. Primary PCR is followed by secondary PCR with nested primers. Only DNA fragments carrying different adaptors at each end tend to amplify exponentially.

cDNA previously amplified with the cDNA Synthesis Kit was purified and digested with RsaI. The digested cDNA was cleaned up with the PCR Purification Kit (Qiagen), eluted into 50 µl of elution buffer, and ethanol precipitated, and adaptors ligated to the tester DNA. In the first hybridization, 13 ng of adaptor-ligated tester was mixed with 147 ng of driver in two separate reactions (each reaction with adaptor 1 and 2R, respectively) and, after denaturation (98° C. for 1.5 min), were allowed to anneal for 9 hr at 68° C. After this first hybridization, the two reactions were combined in the presence of 98 ng of denatured fresh driver and a second hybridization performed for 16 hr at 68° C. Amplification of tester-tester hybrids was performed as described in PCR Purification Kit manual. Efficiency of the ligation to the adaptors and of the subtraction was tested and confirmed as called for in the protocol, using two primers (5'-GTTGATCTCCAAGATCCGTGAGG-3' (SEQ ID NO. 1) and 5'-GTTTCGTCCGAGTTCTCGAC-3') (SEQ ID NO. 2) specific to the β-tubulin gene (tub2).

Upon completion of suppression subtractive PCR, a portion of the product mixture was ligated into pCR®4Blunt-TOPO®, using the Zero Blunt TOPO PCR Cloning Kit (Invitrogen, Carlsbad, Calif., USA), and electroporated into TOP10 cells provided with the kit, to obtain a subtracted expressed sequence tag (EST) bank. Another portion was used to generate hybridization probe PCR-labeled with digoxigenin (DIG) following the protocol of the manufacturer (Roche-Boehringer, Indianapolis, Ind., USA).

cDNA Library Construction.

cDNA synthesis and library construction were performed with the SMART™ cDNA Library Construction Kit (Clontech) according to the manufacturer's instructions. First-strand cDNA was synthesized with the same amount of RNA as used in the cDNA synthesis for the subtraction, and 2 μl undiluted first-strand reaction was used as template to amplify the cDNA. The amplified cDNA was digested with SfiI, size fractionated for removal of low-molecular-size (<0.1 kb) cDNA, and ligated into λTriplEx2 vector (Clontech). cDNA ligated into vector was added to λ phage Gigapack III Gold packaging extract (Stratagene, La Jolla, Calif., USA), and titered in $E.\ coli$ strain XL1-Blue as specified by the manufacturer. For cDNA library amplification, overnight cultures of XL1-Blue were inoculated with an amount of packaged phage suspension to yield $1.0 \times 10^5$ pfu per 150 mm plate (Falcon); in total, 15 plates were prepared, so the amplified library was derived from $1.5 \times 10^6$ primary clones. After incubation overnight at 37° C., to each plate was added 12 ml of λ dilution buffer (100 mM NaCl, 10 mM $MgSO_4$, 35 mM Tris-HCl, pH 7.5, 0.01% gelatin), followed by 20 hr incubation at 4° C. The phage suspensions were then titered for each plate. Since differences in titer between plates would affect representation of cDNA clones in the final amplified library, the appropriate volume of each suspension was determined so that, when combined, each plate contributed equally to the total number of pfu in the pooled library. After pooling, the titer of the amplified library was $5.4 \times 10^9$ pfu $ml^{-1}$.

Southern Blot and PCR Analysis of Genomic DNA.

Fungal genomic DNA was isolated by the method of Al-Samarrai & Schmid, 2000, *Lett. Appl. Microbiol.* 30: 53–56. Because *Neotyphodium occultans* does not grow autonomously in culture, DNA from the *Lolium multiflorum-N. occultans* symbiotum was isolated by the method of Doyle and Doyle, 1990, Focus 12: 13–15 for PCR analysis.

Probes for Southern-blot, dot-blot and cDNA-based northern-blot hybridizations were labeled with DIG as described above. Total subtracted cDNA was labeled by using the primary PCR product in the subtraction as template and the nested PCR primers supplied with the PCR-Select™ cDNA Subtraction Kit (Clontech). Probe for lolA was a labeled 523 bp fragment generated by PCR using primers lolA-5' (5'-GTCTGGCGAATTCTACAGACACG-3') (SEQ ID NO. 3) and lolA-3' (5'-GATGGCCATGTGAG-GAAAGAG-3') (SEQ ID NO. 4). A labeled 1427 bp fragment of the lolC gene was generated by PCR with primers lolC-5' (5'-CGGTGCGCGTCTTCTAAACTTGAC-3') (SEQ ID NO. 5) and lolC-3' (5'-GAATCTTTCCGATG-CAAGGCTTACG-3') (SEQ ID NO. 6).

cDNA-based northerns were performed with complete cDNA, which was gel fractionated and Southern blotted to Hybond™-N+ nylon membranes (Amersham Pharmacia Biotech). Southern blotting of DNA by alkaline transfer, as well as dot blotting onto Hybond™-N+ nylon membranes (Amersham Pharmacia Biotech) and DNA hybridizations were accomplished with standard protocols (Ausubel et al., 2001). Membranes were washed with 0.1×SSC, 0.1% SDS, once for 15 min at room temperature, then for 20 min and again for 30 min at 75° C. (membranes with cDNA) or at 65° C. (membranes with genomic DNA). Chemiluminescent detection of probes hybridized to DNA with anti-DIG antibodies was performed according to the protocol of the supplier (Roche-Boehringer). To visualize labeled probes hybridizing to DNA, membranes were exposed to Hyperfilm™ ECL™ Chemiluminescence film (Amersham Pharmacia Biotech).

PCR screening for lolA was performed on endophyte genomic DNA with primers lolA-3' and lolA-5'. PCR screening for lolC employed primers lolC-3'a (5'-GGTCTAGTATTACGTTGCCAGGG-3') (SEQ ID NO. 7) and lolC-5'a (5'-GTTGCCCACGGTGCGCGTCTTC-3') (SEQ ID NO. 8). PCR was performed with 35 cycles of 95° C. for 30 s, 62° C. for 30 s, and 72° C. for 1 min. As a positive control for DNA integrity in this screening, a tub2 gene fragment was amplified by PCR with primers 5'-TG-GTCAACCAGCTCAGCACC-3' (SEQ ID NO. 9) and 5'-GAGAAAATGCGTGAGATTGT-3' (SEQ ID NO. 10) (Byrd et al., 1990), with 35 cycles of 95° C. for 30 s, 55° C. for 30 s, and 72° C. for 1 min.

cDNA Library Screening and Conversion of Phage to Plasmid Clones.

Screening of the cDNA library was essentially as described by Ausubel et al. (2001). Phage were plated in a lawn of *E. coli* XL1-Blue, and phage lifts were on Hybond™-N+ nylon membranes (Amersham Pharmacia Biotech). To convert clones in λTriplEx2 to plasmid form, plaques were added to *E. coli* strain BM25.8 (which expresses Cre-recombinase) as per the supplier's protocols (Clontech). Single, isolated colonies were selected on LB agar with ampicillin, picked and grown in LB with ampicillin, and plasmids isolated by a rapid alkaline procedure (Ahn et al., 2000, *BioTechniques* 29: 266–368). To verify that a plasmid carried the desired insert, 3 μl of each plasmid was spotted onto a nylon membrane for dot blotting, and the membrane hybridized to the probe initially used to identify the λ-phage clone.

Plasmid DNA Isolation, Sequencing, and Database Search of cDNAs.

Plasmid DNA was isolated from bacterial cells by the rapid alkaline miniprep procedure (Ahn et al., 2000). Plasmid inserts were sequenced with primers L-triplEx 5' (5'-TCCGAGATCTGGACGAGC-3') (SEQ ID NO. 11) and L-triplEx 3' (5'-TAATACGACTCACTATAGGG-3') (SEQ ID NO. 12), specific to vector regions flanking the cDNA inserts. DNA cloned into TOPO vector (Invitrogen) was sequenced with M13-reverse (5'-CAGGAAACAGCTAT-GAC-3') (SEQ ID NO. 13) and M13-forward (5'-GTAAAACGACGGCCAG-3') (SEQ ID NO. 14) primers. Sequencing of DNA was performed with the BigDye Terminator Cycle Sequence Kit (Applied Biosystems) on an ABI 310 automated sequencer (Applied Biosystems) or, for high-throughput sequencing, the CEQ2000XL DNA Analysis System (Beckman-Coulter, Fullerton, Calif., USA) with the CEQ™ DTCS—Quick Start Kit (Beckman-Coulter). DNA sequences obtained were entered into the basic local alignment search tool (BLAST; Altschul et al., 1997) programs at the National Center for Biotechnology Information site (NCBI; http://www.ncbi.nlm.nih.gov/BLAST/) to search the nonredundant nucleic acid (nr) database, and at the Whitehead Institute site (http://www-genome.wi.mit.edu/annotation/fungi/neurospora/) to search the *Neurospora crassa* database for similar sequences. Matches with known DNA/protein sequences in these databases were considered significant at $E \leq 10^{-4}$. Predicted protein sequences were analyzed for occurrence of biologically significant sites by searching the database of protein families and domains (PROSITE) at ExPASy (Expert Protein Analysis System; http://ca.expasy.org/).

EXAMPLE 2

Transcripts Up-Regulated in Loline Alkaloid-Producing Cultures.

Figure 2:
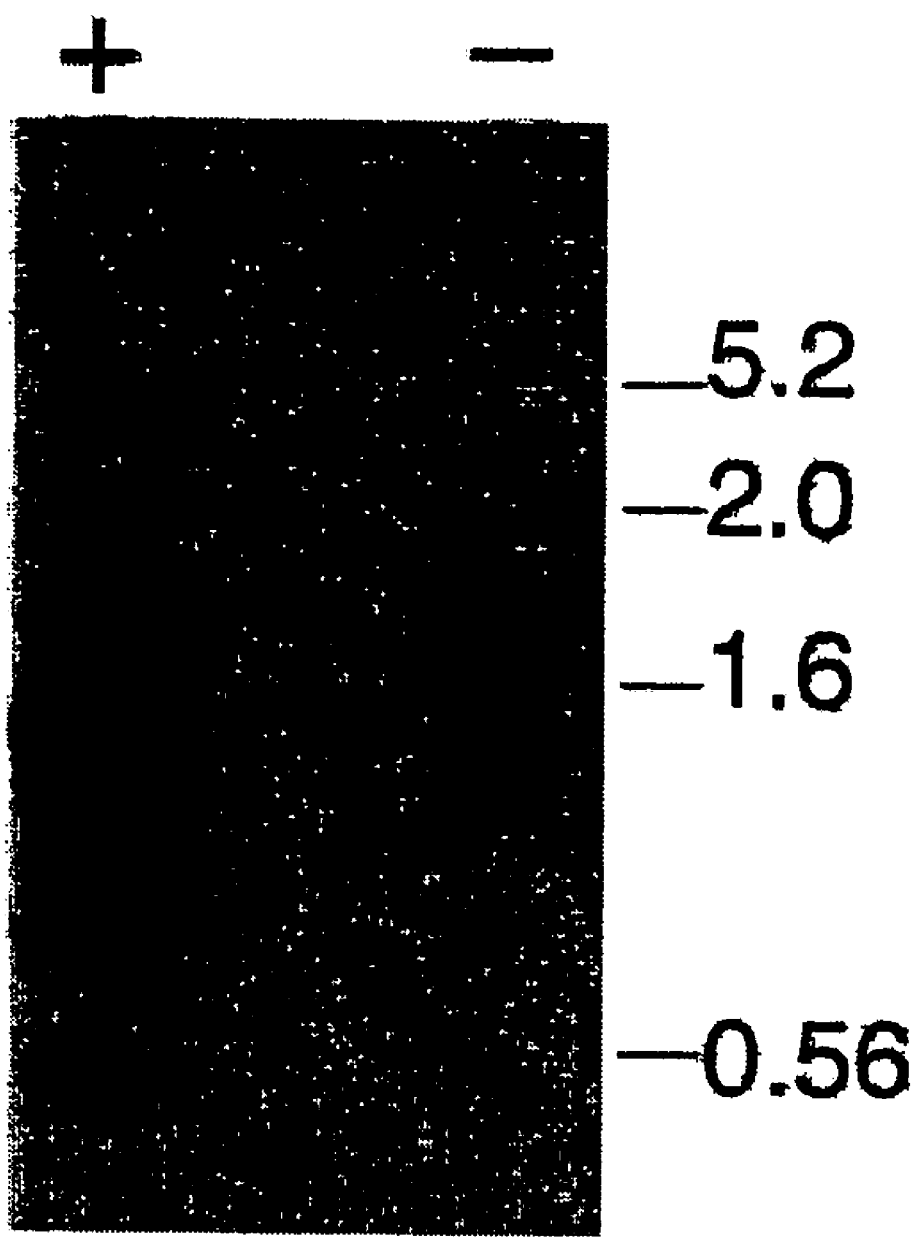
FIG. 2 is an autoradiograph showing expression of transcripts isolated in the suppression subtractive hybridization in loline-producing (+) and suppressed (−) cultures. In each lane was loaded 0.5 µg of total cDNA synthesized from total RNA and probed with subtracted cDNA; molecular sizes indicated (in kilobases) correspond to molecular marker (HindIII/EcoRI-cut λ.DNA) run on the same gel.

To gauge the success of the suppression subtractive hybridization, and to get an overview of the number and sizes of cDNAs potentially enriched by the subtraction, cDNA-based northern analysis on total cDNA from the cultures were conducted (FIG. 2). The subtracted cDNAs hybridized much more strongly with total cDNA from the LA-producing cultures than to total cDNA from the suppressed cultures, demonstrating enrichment of cDNAs up-regulated in the LA-producing cultures. Multiple sizes of cDNAs hybridized with the subtracted cDNAs, indicating up-regulated expression of several different genes in the LA-producing cultures.

The λTriplEx2 library created with complete cDNA from LA-producing cultures contained a total of $4.1 \times 10^6$ primary pfu. From this, $1.5 \times 10^6$ primary pfu, likely representing the complete cDNA population obtained from the LA-producing cultures, were amplified to $5.4 \times 10^9$ pfu ml$^{-1}$.

The number of recombinant clones (=likely containing cDNA inserts) in the unamplified library was assessed by blue-white screening of the plated library at $3.3 \times 10^6$ pfu (>80% of all primary library clones). To determine the percentage of library clones that contained transcripts up-regulated in the LA-producing cultures, phage lifts were probed with total subtracted cDNA. Approximately 5.3% of all clones (about 6.6% of the presumed recombinant clones) hybridized with the subtracted cDNA (data not shown).

EXAMPLE 3

Several Subtracted cDNA Similarities with Database Sequences.

Twenty clones from the subtracted EST bank, and six library clones hybridizing to total subtracted cDNA were sequenced. In the suppression subtractive method incomplete suppression can result from amplification of tester-tester hybrids which have only one of the two adaptors at each end. However, all ESTs sequenced from the bank of subtracted cDNAs had the two different adaptors at their ends, indicating that contaminating background due to non-specific amplification of tester was very low.

Sequences of subtracted cDNA clones, as well as inserts in library clones that hybridized to subtracted cDNAs, were used to query databases by various BLAST algorithms. For several subtracted cDNAs (Table 1) and cDNAs from the λ-library (Table 2), matches to known protein sequences in NCBI, or sequences in the *Ns. crassa* database were identified. Five library and subtracted clones had significant similarity to the C-terminal amino acid regions of aspartate kinases (Tables 1 & 2). Two of the library clones with similarity to aspartate kinase were identical to each other in sequence (P2 and P16). However, a third library clone (P17) differed from the other two (94% identity), but had 100% sequence identity with two subtracted clones (B8 and C5). The detected variation in sequence among the clones suggested more than one form of this gene in *N. uncinatum*. The presence of two genomic alleles of the AspK-related gene in *N. uncinatum* was verified by PCR with primers with allele-specific nucleotides at their 3'-ends (data not shown). Because other results of this study (described below) strongly associate these sequences with LA production, we will hereafter designate the corresponding genes as lolA alleles; the two allelic sequences have been submitted to GenBank (accessions AF439396 and AF439395).

The predicted proteins (209 and 210 aa) encoded by lolA alleles were smaller than known aspartate kinases (which usually exceed 500 aa) and had similarity only to the C-terminal regions of aspartate kinases. This was indicated by protein sequence alignments with known aspartate kinases that gave the most significant matches in BLAST. These proteins, from *Schizosaccharomyces pombe* and *Saccharomyces cerevisiae* (GenBank accessions T39822 and P10869), aligned with a region starting at amino acid position 47 and ending at amino acid 204 of the predicted lolA proteins and had 25–26% identity to lolA, but only within a region of the known aspartate kinases starting at about amino acid 351 and ending at amino acid 495. PROSITE searches with the predicted amino acid sequences of the two lolA alleles indicated that both lacked the aspartate kinase signature, defined by PROSITE as [LIVM]-x-K-[FY]-G-G-[ST]-[SC]-[LIVM], a conserved region located near the N-terminal end of aspartate kinases.

One subtracted clone, D6 (Table 1), gave highly significant matches with fungal (*Ns. crassa, Emericella nidulans,* and *S. cerevisiae*) genes for O-acetylhomoserine-(thiol)lyase (homocysteine synthase), and the related enzymes, cystathionine γ-synthase and cystathionine β-lyase, all of which are γ-type pyridoxal phosphate-containing enzymes in sulfur-containing amino acid biosynthesis and interconversion pathways. Additionally, significant similarity was found with an enzyme in the biosynthesis of the bacterial compound rhizobitoxine. The molecular size of the transcript (between 1.5 to 2 kb, FIG. 3) predicted a protein similar in size to known homocysteine synthases, which are 430–450 amino acids (Sienko et al., 1998). A related sequence was recently identified at a locus associated with LA production in *Epichloë festucae* (Wilkinson et al., 2000; Spiering et al., 2000). Because these data and further evidence presented below associated this sequence with LA production, the corresponding gene was designated lolC (GenBank accessions AF461175, AF461176).

TABLE 1

Matches of subtracted cDNA clones with sequences in non-redundant (nr) and *Neurospora crassa* database BLAST searches.

| Clones[1] | Length in bp | nr matches, identify (%), and E values | *Ns. crassa* matches, identity (%), and E values |
|---|---|---|---|
| K8, C37, D5 | 468 | —[2] | — |
| B8, C5[3] | 633 | *Sc. pombe*[4] aspartate kinase gene, 24%, 5e–07 | — |
| N17, C7 | 1521 | — | — |
| C2, D1 | 724 | Krüppel-like C2H2 zinc finger transcription factors, 44%, 7e–08 | various contigs (1.246; 1.392; 1.622; 1.686; 1.151), 35–52%, 4e–20 to 1e–05 |
| C1, C3 | 283 | — | — |
| E21 | 388 | — | — |
| A6 | 370 | — | — |
| A7 | 379 | — | — |
| A8 | 554 | — | Contig 1.291 (57.61–57.83 kb), 56%, |
| C8 | 430 | *Sc. pombe* hypothetical protein, 42%, 2e–05 | Contig 2.503 (15.96–16.19 kb)., 38%, 7e–07 |
| D2 | 472 | — | — |
| D3 | 269 | — | — |
| D4 | 694 | rRNA intron-encoded homing endonuclease, 86%; 2e–11 | various contigs (2.820; 2.798; 2.816; 2.793; 2.790; 2.943; 2.796, 2.843; 2.831; 2.957), 46–53%, 4e–10 to 3e–08 |
| D6[5] | 374 | homocysteine synthase/O-acetylhomoserinesulfhydrolase, 53%, 1e–22; related enzymes in methionine/cysteine biosynthesis, <1e–07); RtxA, enzyme in rhizobitoxine biosynthesis, 37%, 1e–10 | Contig 2.65, 54%, 3e–24; Contig 2.688, 34%, 3e–11 |

[1]Listed in order of frequency from most common to least common.
[2]— = No significant match.
[3]lolA clones.
[4]*Schizosccharomyces pombe*.
[5]lolC clone.

TABLE 2 cDNA library clones hybridizing to total subtracted cDNA.

| Clone/s | Length of nucleotide sequence [bp] | Length of putative ORF [aa] | Identical in sequence to subtracted clones/s | BLAST matches, identify (%), and E values |
|---|---|---|---|---|
| P2, P16[6] | 838, 880[7] | 210 | none | aspartate kinase (*Sc. pombe*) 25%, 3e–07 |
| P3 | 446 | 35 | K8, C37, D5 | —[8] |
| P15 | 725 | 111 | none | *Ns. crassa* contig 1.1526 (36.73–36.96 kb), 36%, 5e–10 |
| P17 | 774 | 209 | B8, C5 | aspartate kinase (*Sc. pombe*), 24%, 5e: 07 |
| P18 | 449 | 30 | none | |

[6]lolA clones
[7]Difference in length of 3' untranslated region.
[8]— = No significant match.

EXAMPLE 4

Association of the lolA and lolC Genes with Loline Production.

Figure 3:
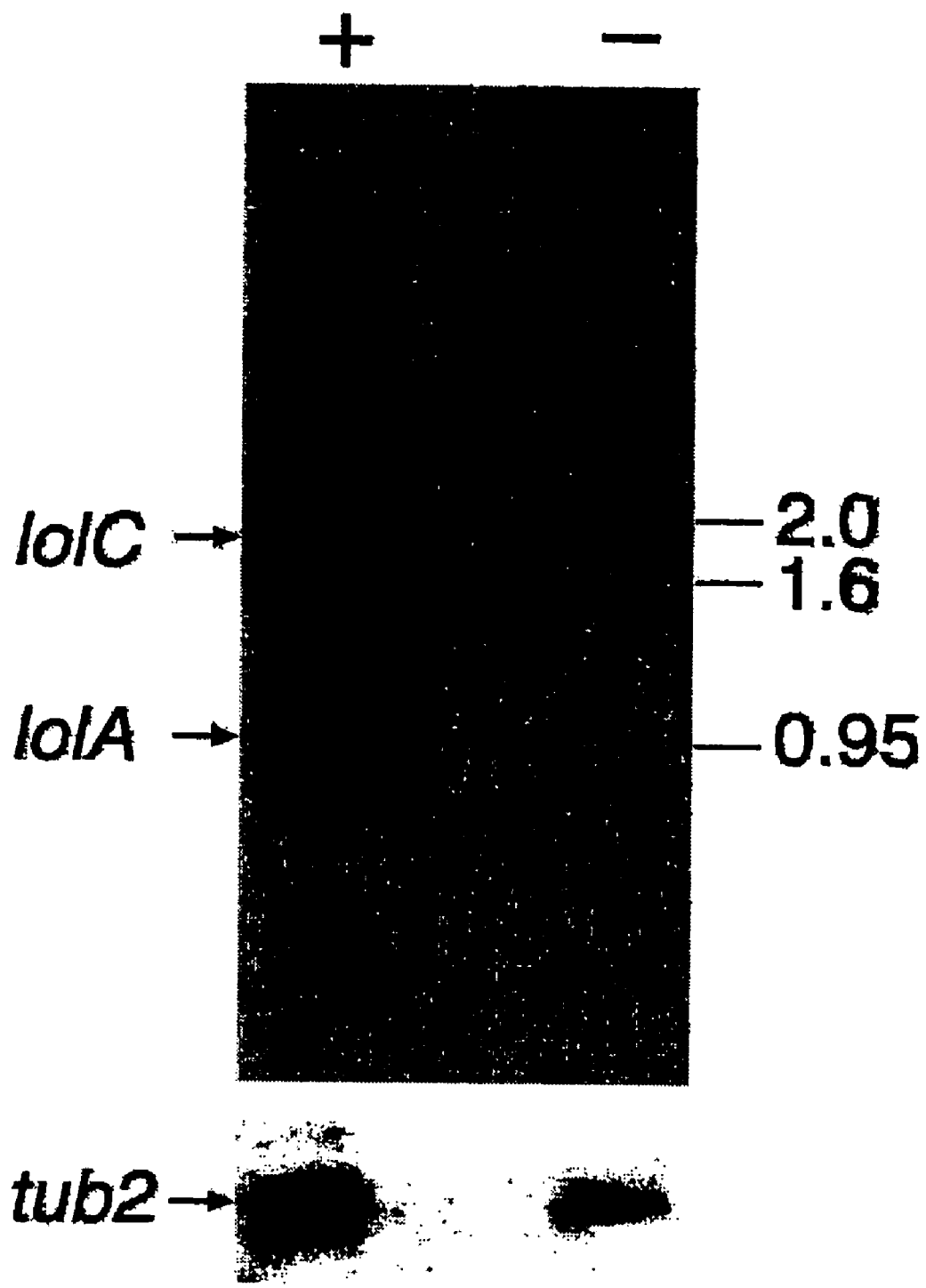
FIG. 3 is an autoradiograph showing expression of lolA and lolC genes in LA-producing (+) and suppressed (−) cultures. In each lane was loaded 0.5 µg of total cDNA synthesized from total RNA. cDNAs were probed with a mixture of a labeled 523 bp fragment from lolA and a labeled 1427 bp fragment from lolC. Identities of the hybridizing bands were confirmed in separate experiments with the individual probes (data not shown). Bottom panel shows expression of the tub2 as a control. Molecular sizes (in kilobases) are indicated, and correspond to bands of a DNA-size marker (HindIII/EcoRI-cut λDNA) run in the same gel.

Genomic sequences of lolC and one allele of lolA (clone P1.7) were obtained by using primers based on the cDNA of the lolA gene and genomic sequence of the lolC gene from *E. festucae* (data not shown). This information was used to design primers for specific probes and detection of lolA and lolC sequences in cDNA-based northern analysis of complete cDNAs from LA-producing and suppressed cultures (FIG. 3). Both sequences were expressed in the LA-producing cultures. Strong hybridizing bands were detected from the complete cDNA from LA-producing cultures, whereas faint bands were obtained from the complete cDNA from the suppressed cultures.

Figure 4:
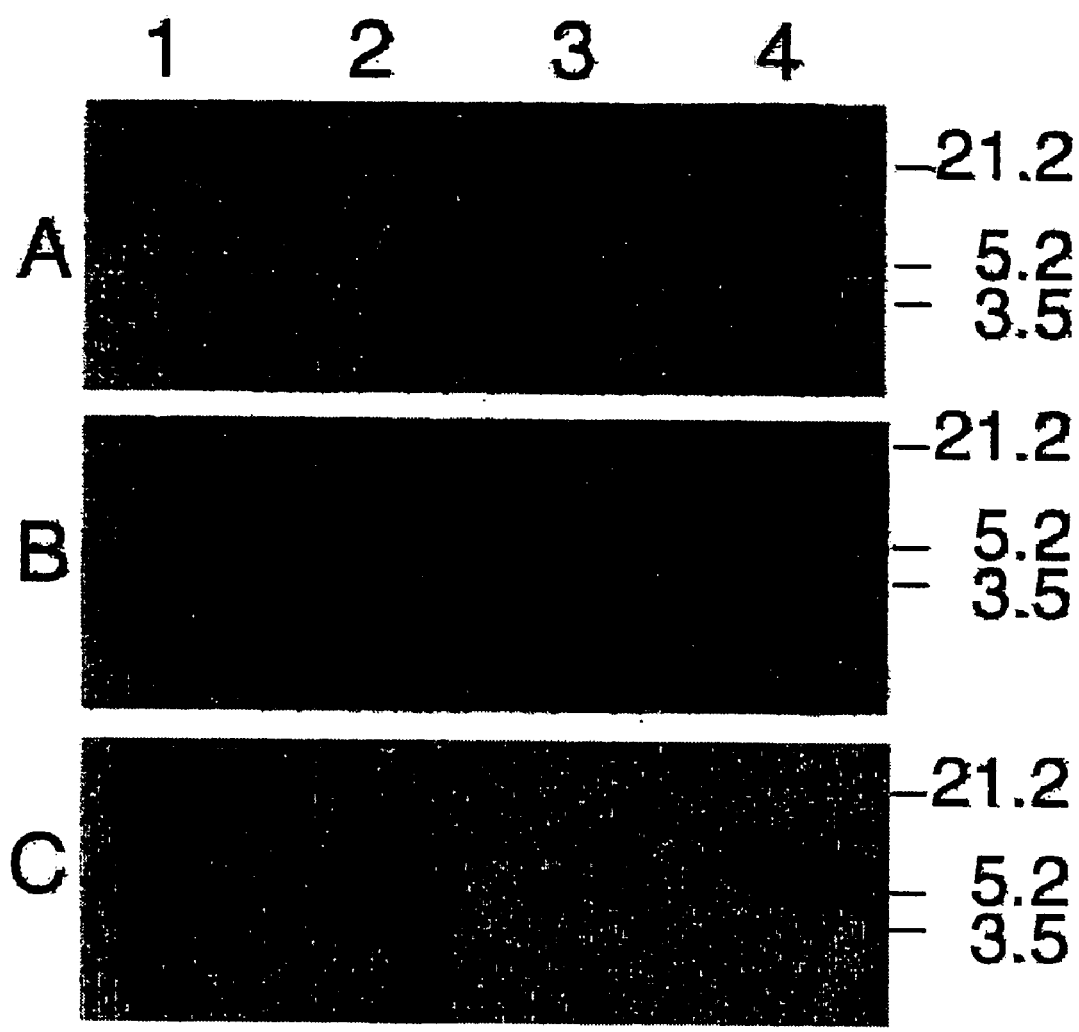
FIG. 4 is a Southern blot of HindIII-digested genomic DNAs probed for lolA (panel A), lolC (panel B), and tub2 (panel C). Genomic DNAs were from *N. lolii* 138 (lane 1), *E. festucae* CBS 102477 (lane 2), *E. festucae* CBS 102475 (lane 3), and *N. uncinatum* CBS 102646 (lane 4). Numbers adjacent to each blot indicate band sizes (in kilobases) of the molecular marker run in the same gel. For LA phenotype of each species/isolate see Table 3.

LA production is a trait specific to endophyte species (Christensen et al., 1993; Siegel et al., 1990; TePaske and Powell, 1993) or even isolates within species (Wilkinson et al., 2000). Consequently, we reasoned that genes associated with LA production would be present in all LA-producing endophytes, but might be absent from endophytes that do not produce LA. For many endophyte species and isolates available from our collection the LA phenotypes were known from the literature (Table 3), and these were confirmed by GC analyses of plants symbiotic with these endophytes. Additional species or isolates included in this survey were similarly assessed for LA production (Table 4). In Southern-blot analysis of genomic DNAs from two LA producers and two nonproducers, lolA and lolC sequences hybridized only with DNA from the endophytes that produce LA (FIG. 4). The probes used to detect lolA and lolC did not have sites for the restriction enzyme used in the genomic digests, so for each putative allele one hybridizing band was expected. In *N. uncinatum*, two bands were observed from the genomic DNA probed with lolA, indicating at least two alleles of this gene; hybridization with lolC gave only one band, suggesting only one allele of this gene was present, but the possibility that this single band represented multiple alleles of lolC could not be excluded. In *E. festucae*, hybridization with the two probes gave one strong hybridizing band for each, suggesting one allele of each gene. The additional, fainter hybridizing bands present on the blots corresponded to some bands on the ethidium bromide-stained gel (not shown) and were, therefore, likely due to non-specific binding of the probes to mitochondrial or repetitive genomic DNA.

Figure 5:
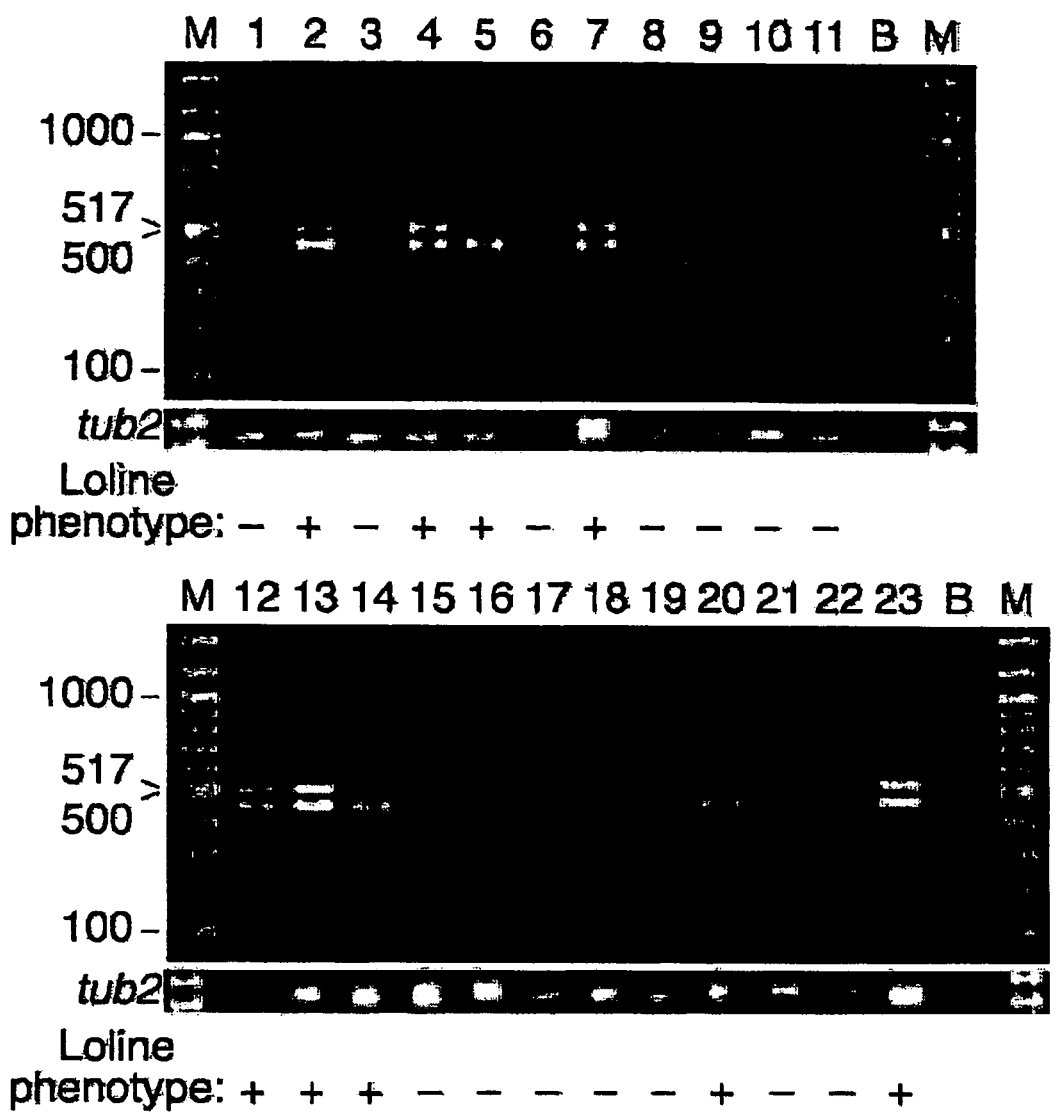
FIG. 5 demonstrates the presence of the lolA and lolC genes in endophyte species and isolates differing in LA production. Shown are electropherograms with 2 µl of PCR product loaded in each lane. The multiplex PCR generated a 523 bp product from lolA and a 461 bp product from lolC. The control PCR generated a 726 bp product from tub2. Numbers above each lane indicate species or isolate listed under the same number in Table 3; lanes B were PCR blanks run without added template DNA; lanes M are molecular size markers (sizes indicated in bp).

Diagnostic PCR was used with primers specific to the lolA and lolC genes for detection of these sequences in all species and isolates listed in Table 3. Detection of the lolA and lolC genes in endophytes was strictly associated with the LA-producing phenotype (FIG. 5). In addition, the two genes were detected in *N. chisosum* (ATCC 64037).

The high expression of lolA and lolC in LA-producing cultures of *N. uncinatum*, and the strict correlation of LA production with presence of the two genes in the different endophytes, lent strong support to involvement of the lolA and lolC genes in LA production.

TABLE 3

LA phenotype of endophyte species and isolates used in this study. Indicated are the respective grass hosts which were used in the determination of the LA, and from which the endophytes in this study were originally isolated.

| Species/isolate[9] | Grass host | Loline phenotype[10] | Reference[11] |
|---|---|---|---|
| 1)[12] *Epichloë festucae* CBS 102477 | *Festucae rubra* | − | 1 |
| 2) *E. festucae* CBS 102475 | N/A[13] | + | 2 |
| 3) *E. typhina* 8 | *Lolium perenne* | − | 3 |
| 4) *Neotyphodium aotearoae* CBS 109345 | *Echinopogon ovatus* | + | 4 |
| 5) *N. aotearoae* ATCC MYA-1231 | *E. ovatus* | + | 4 |
| 6) *N. australiense* CBS 109346 | *E. ovatus* | − | 4 |
| 7) *M coenophiolum* ATCC 90664 | *Lolium arundinaceum* | + | 3 |
| 8) *N. huerfanum* ATCC 604040 | *Festuca arizonica* | − | 3 |
| 9) *N. inebrians* 818 | *Achnatherum inebrians* | − | 5 |
| 10) *N. lolii* 138 | *L. perenne* | − | 3 |
| 11) *N. melicicola* CBS 109342 | *Melica decumbens* | − | 4 |
| 12) *N. occultans* 999 | *Lolium multiflorum* | + | 6 |
| 13) *N. siegelii* ATCC 74483 | *Lolium pratense* | + | 7 |
| 14) Neotyphodium sp. 55 | *Poa autumnalis* | + | 3 |
| 15) Neotyphodium sp. 87 | *Festuca paradoxa* | − | 3 |
| 16) Neotyphodium sp. LpTG-2 Lp1 | *L. perenne* | − | 8 |
| 17) Neotyphodium sp. 269 | *Hordeum bogdanii* | − | 4 |
| 18) Neotyphodium sp. 270 | *Hordeum brevisubulatum* | − | 4 |
| 19) Neotyphodium sp. 361 | *Hordelymus europaeus* | − | 9 |
| 20) Neotyphodium sp. FaTG-3 Tf18 | *L. arundinaceum* | + | 4 |
| 21) Neotyphodium sp. FaTG-2 Tf14 | *L. arundinaceum* | − | 4 |
| 22) Neotyphodium sp. 4096 | *Achnatherum robustum* | − | 4 |
| 23) *N. uncinatum* CBS 102646 | *L. pratense* | + | 7 |

Figure 6:
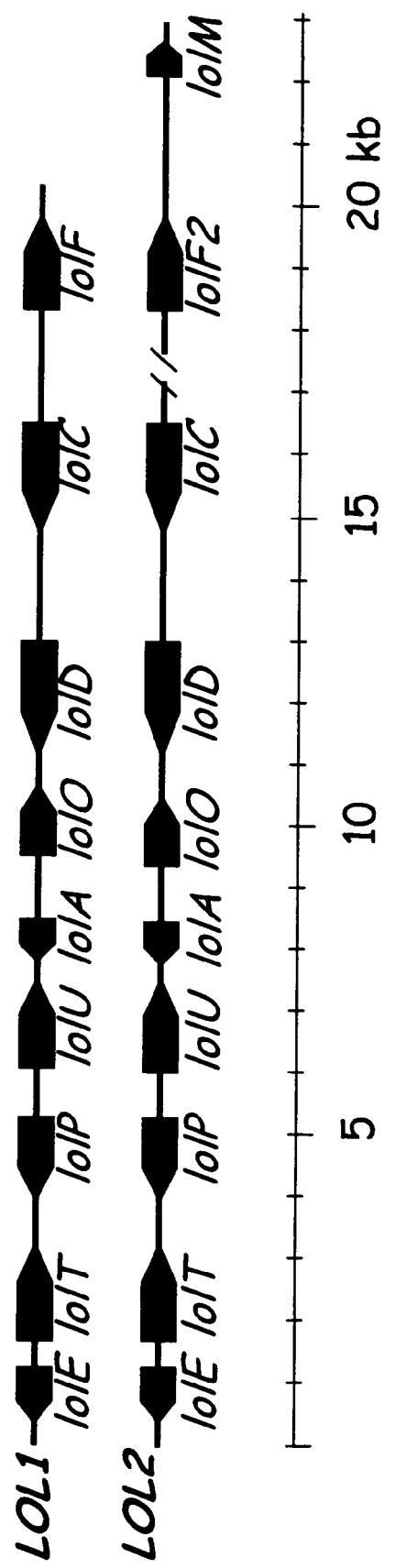
FIG. 6 illustrates the *N. uncinatum* lol clusters 1 (LOL1) (upper bar) and 2 (LOL2) (lower bar). It appears that the lolF2 allele and lolM are linked to LOL2.

[9]CBS = Centraalbureau voor Schimmelcultures, Fungal Biodiversity Center, Utrecht, The Netherlands (http://www.cbs.knaw.nl), ATCC = American Type Culture Collection, Manassas, Virginia, USA (http://www.atcc.org). Other designations are from the referenced papers or are laboratory isolate numbers.
[10]= "+" = loline-producing, "−" = loline non-producing.
[11]References are (1) Leuchtmann and Schardl (1998), (2) Wilkinson et al. (2000), (3) Siegel et al. (1990), (4) this study (see Table 4), (5) Miles et al. (1996), (6) TePaske and Powell (1993), (7) Craven et al. (2001), (8) Christensen et al, (1993), (9) Leuchtmann et al., (2000).
[12]Numbers before each isolate correspond to the numbers indicated above gel lanes in FIG. 6.
[13]N/A = not applicable. Isolate derived by mating *E. festucae* CBS102477 with an *E. festucae* isolate CBS 102474 from *Lolium giganteum*.

TABLE 4

LA in plants with endophyte species for which the LA phenotype was previously unknown.

| Species/isolate[14] | Host grass | Lolines[15] |
|---|---|---|
| *Neotyphodium aotearoae* CBS 109345 | *Echinopogon ovatus* | 1780 |
| *N. aotearoae* ATCC MYA-1231 | *E. ovatus* | 2120 |
| *N. australiense* CBS 109346 | *E. ovatus* | nd |
| *N. melicicola* CBS 109342 | *Melica decumbens* | nd |
| Neotyphodium sp. FaTG-3 Tf18 | *Lolium arundinaceum* | 670 |
| Neotyphodium sp. FaTG-2 Tf14 | *L. arundinaceum* | nd |
| Neotyphodium sp. 269 | *Hordeum bogdanii* | nd |
| Neotyphodium sp. 270 | *Hordeum brevisubulatum* | nd |
| Neotyphodium sp. 270 | *Stipa robusta* | nd |

[14]CBS = Centraalbureau voor Schimmelcultures, Fungal Biodiversity Center, Utrecht, The Netherlands (http://www.cbs.knaw.nl), ATCC = American Type Culture Collection, Manassas, Virginia, USA (http://www.atcc.org). Other designations are from the referenced papers or are laboratory isolate numbers.
[15]Reported is the sum of N-formyl and N-acetyl lolines in µg g$^{-1}$ dry weight plant tissue.
nd = not detected (limit of dection = 10 µg g$^{-1}$).

EXAMPLE 5

Additional Subtracted cDNAs Matching Known Genes and Genomic Sequences.

As shown in Tables 1 & 2, several other cDNAs isolated by the subtraction method also gave highly significant matches in BLAST searches of the nr and *Ns. crassa* databases. Matches included a zinc-finger transcription factor, a hypothetical protein in *S cerevisiae*, and a homing endonuclease. Additionally, matches with *Ns. crassa* sequences were identified for putative ORFs of one hybridizing library clone, P15, and one subtracted clone, A8.

A survey of the distribution of the putative zinc-finger transcription factor among eight endophytes differing in LA production (four LA producers and four non-producers) was performed by diagnostic PCR. There was no association of this putative zinc-finger transcription factor gene with LA production; its presence was detected only in two isolates, one LA-producer (*N. uncinatum*) and one non-producer (*N. huerfanum*) (data not shown).

As further indicated in Tables 1 & 2, a number of sequences from library and subtracted clones gave no significant matches with known genes in the nr database and sequences in the *Ns. crassa* genome. For one subtracted clone, N17, the full-length cDNA sequence was obtained by PCR, using an aliquot of the amplified cDNA library and gene and vector-specific primers. A predicted ORF of 363 amino acids was found within the N17 cDNA (data not shown), but this amino acid sequence did not give significant matches with any genes or sequences in the nr and *Ns. crassa* databases or known protein patterns in the PROSITE database.

EXAMPLE 6

Identification of the LOL1 and LOL2 Gene Clusters

Central to the present invention is the identification of the loline alkaloid gene clusters LOL1 (SEQ ID NO. 15), and LOL2 (SEQ ID NO. 16) which apparently may also include lolF2 and lolM (SEQ ID NO: 17). The association in *Neotyphodium uncinatum* of lolA and lolC was tested by long-distance-PCR. The 8.2 kb product contained the expected sequences of both, plus two additional open reading frames between them. We then walked outward from this fragment by vectorette-mediated PCR, and in the process identified two gene clusters (LOL1 and LOL2 in FIG. 6).

In addition to lolC and lolA, at least 8 (LOL1) or 7 (LOL2) ORFs were inferred within LOL1 and LOL2 by using a program with an algorithm for prediction of fungal genes. PCR analyses/Southern hybridization on a cDNA library/total cDNA from *N. uncinatum* showed expression of the ORFs lolM, lolF, lolC, lolO, lolA, and lolE, indicating that these contain active genes. The details of the gene predictions and coordinates, i.e., location of the exons in the ORFs of LOL1 and LOL2 are given below. LOL1 and LOL2 differ in sequence (LOL1 has ~95% nucleotide sequence identity to LOL2), thus represent two truly distinct genomic regions. Altogether, ten genes were inferred in the gene clusters, with most of the genes shared between the clusters. PCR and Southern-blot analyses indicated that all ten genes were unique to the loline alkaloid producers among the isolates surveyed in Table 3 (Fung. Genet. Biol. Spiering et al.). Nine of the genes, lolE, lolT, lolP, lolU, lolA, lolO, lolD, lolC and lolF, were found in two allelic forms.

The amino acid sequences deduced from the LOL gene ORFs gave highly significant matches ($E<10^{-5}$; except lolU and lolM for which $E>0.01$) with known enzyme sequences in the protein databases curated by the National Center of Biotechnology Information (http://www.ncbi.nlm.nih.gov; NCBI). The gene functions predicted by Genbank searches of the databases at NCBI, and gene orientations within the clusters, thereby indicate that LOL2 contains eight genes (i.e., lolE, lolT, lolP, lolU, lolA, lolO, lolD, and lolC) representing alleles of genes present in LOL1. LOL1 contains an additional gene, named lolF, hitherto not found in LOL2. The genomic location of the additional ORFs, lolF2 and lolM, relative to the two LOL clusters is presently unknown, but we postulate that lolF2 and lolM are located close to LOL2. lolF2 and sequence adjacent to it has ~93% identity to lolF (and sequence adjacent to it) in cluster LOL1.

The LOL1 gene cluster spans about a 25.3 kB region and consists of 9 ORFs. Open reading frames of LOL1 are indicated relative to nucleotide numbers annotated to SEQ ID NO: 15; mRNA sequences of each gene are given by joined exons determined by cDNA sequencing or predicted by the fgenesh (*Neurospora*) gene prediction program at "Softberry", http://www.softberry.com/berry.phtml?topic=gfind); gene orientations are indicated by "+" (forward strand) and "−" (reverse strand).

ORF1 of LOL1 is lolE: +strand, join 23457–24195, 24275–24306 (predicted by fgenesh at Softberry).

ORF2 of LOL1 is lolT: −strand, join 23003–22916, 22838–22916, 22420–22246, 22170–21486 (predicted by fgenesh at Softberry).

ORF3 of LOL1 is lolP: +strand, join 19245–19554, 19639–20225, 20287–20694, 20818–20846, 20919–21045 (predicted by fgenesh at Softberry).

ORF4 is lolU: −strand, join 17377–17023, 16832–15889 (predicted by fgenesh at Softberry).

ORF5 of LOL1 is lolA: +strand, join 14951–15476, 15545–15648 (determined by sequencing of lolA cDNA).

ORF6 of LOL1 is lolO: −strand, join 13961–13770, 13781–13677 (predicted by fgenesh at Softberry).

ORF7 of LOL1 is lolD: +strand, join 10462–10588, 10945–11115, 11194–11757, 12211–12240, 12376–12383 (predicted by fgenesh at Softberry).

ORF8 of LOL1 is lolC: +strand, join 6903–7000, 7063–7114, 7199–7282, 7364–7723, 7810–8364, 8435–8709 (determined by sequencing of lolC cDNA).

ORF 9 of LOL1 is lolF: −strand, join 5095–5028, 4960–3509, 3448–3346 (predicted by fgenesh at Softberry).

The LOL2 gene cluster spans about a 16.4 kB region and consists of at least 8 ORFs. It appears that LOL2 may include lolF2 and lolM (SEQ ID NO: 17) linked to the 5' end of SEQ ID NO: 16, in which case the LOL2 gene cluster would span about a 24 kB region, consisting of 10 ORFs (i.e., ORF1' through ORF10'). ORFs of LOL2 are indicated relative to nucleotide numbers annotated to SEQ ID NO: 16; mRNA sequences of each gene are given by joined exons determined by cDNA sequencing or predicted by the fgenesh (*Neurospora*) gene prediction program at "Softberry", http://www.softberry.com/berry.phtml?topic=gfind); gene orientations are indicated by "+" (forward strand) and "−" (reverse strand).

ORF1' of LOL2 is lolE: +strand, join 15210–15946, 16026–16057 (predicted by fgenesh at Softberry).

ORF2' of LOL2 is lolT: −strand, join 14753–14666, 14588–13997, 13920–13206 (predicted by fgenesh at Softberry).

ORF3' of LOL2 is lolP: +strand, join 11163–11257, 11551–11762, 11836–11925, 12000–12541 (predicted by fgenesh at Softberry).

ORF4' of LOL2 is lolU: –strand, join 10438–9597, 9531–8916 (predicted by fgenesh at Softberry).

ORF5' of LOL2 is lolA: +strand, join 8006–8534, 8603–8706 (predicted by sequencing of lolA cDNA).

ORF6' of LOL2 is lolO: –strand, join 7190–6999, 6907–6011 (predicted by fgenesh at Softberry).

ORF7' of LOL2 is lolD: +strand, join 3867–3993, 4103–4525, 4616–5026, 5118–5143 (predicted by fgenesh at Softberry).

ORF8' of LOL2 is lolC: +strand, join 873–970, 1033–1084, 1167–1250, 1334–1693, 1782–2335, 2406–2679 (predicted by sequencing of lolC cDNA).

It also appears that LOL2 may include lolF2, an allele of lolF, and lolM, probably linked to the 5' end of LOL2 (SEQ ID NO: 16). The ORFs of lolF2 and lolM are indicated relative to nucleotide numbers annotated to sequence of SEQ ID NO: 17; mRNA sequences of each gene are given by joined exons predicted by the fgenesh (*Neurospora*) gene prediction program at "Softberry", http://www.softberry.com/berry.phtml?topic=gfind); gene orientations are indicated by "+" (forward strand) and "–" (reverse strand).

ORF9' is lolF2: –strand, join 5804–4342, 4281–4207, 3905–3821 (predicted by fgenesh at Softberry).

ORF10' is lolM: –strand, join 1689–1525, 1430–1332, 1231–1174, 1085–1021 (predicted by fgenesh at Softberry).

EXAMPLE 7

Functional Assignment of the Loline Alkaloid Gene Clusters

Most of the predicted gene products show highly significant BLAST matches (E 1e-7) with known biosynthetic enzymes and motifs. The closest BLAST matches and/or motifs of the ten genes follow in the order that they occur in the clusters: lolE gave a match to epoxidases; lolT and lolT2 matched the diagnostic domain of α-type pyridoxal phosphate (PLP)-associated enzymes, including class-v aminotransferases; lolP matched cytochromes P450, with closest relationship to pisatin demethylase from *Nectria haematococca*; lolU gave no significant match or diagnostic motif; lolA closely matched the Asp kinase allosteric amino acid binding domain; lolO matched nonheme-Fe oxidoreductases, especially isopenicillin N synthase; lolD matched ornithine decarboxylase (an α-type PLP enzyme); lolC appeared to be a γ-type PLP enzyme; lolF and lolF2 appeared to encode an FAD-containing monooxygenase with closest match to cyclohexanone oxidase; lolM had no significant BLAST match or motif.

EXAMPLE 8

Hybridizable Variants

The nucleic acids of the present invention comprise at least a nucleotide sequence of all or part of SEQ ID NO: 15 or SEQ ID NO: 16 or variants thereof. It also appears that SEQ ID NO: 17 or variants thereof may be part of the LOL2 gene cluster linked to the 5' end of SEQ ID NO: 16, and therefore, nucleic acid sequences that hybridize to all or part of SEQ ID NO: 17 are also encompassed by the present invention. Variants of the present invention encode isolated nucleic acids that at least hybridize to all or part of SEQ ID NO. 15 or SEQ ID NO. 16 or the complements thereof under hybridization conditions of, at, or between, low and high stringency conditions, and have insecticidal activity. Low stringency conditions are generally about 3×SCC at about 45° C. to about 65° C., and high stringency conditions are generally about 0.1×SSC, 0.1% SDS at about 65° to 68° C. Preferably, the hybridization conditions are highly stringent at 0.1×SSC, 0.1% SDS at 65° C. Variants are made by methods known to one of ordinary skill in the art and as set forth in Maniatis et al. Molecular Cloning: A Laboratory Manual (Current Edition). Preferably, the hybridized nucleic acids code for a polypeptide that has one or more or all of the physical and/or biological properties of loline alkaloids, such as insecticidal activity and feeding deterrent properties.

EXAMPLE 9

Host-Vector System

Identification and cloning of the loline alkaloid gene clusters is useful for the development of a host-vector system for the efficient recombination production of both novel and known alkaloids. The coding sequences which collectively encode a loline-type alkaloid gene cluster, including variants, hybrids, mutants, analogs or derivatives of the loline alkaloid gene cluster, can be inserted into one or more expression vectors, using methods known to those of skill in the art. The replacement gene cluster need not correspond to the complete native loline alkaloid gene cluster, but need only encode a functional gene cluster to catalyze production of an alkaloid.

The recombinant vector(s) of the present invention includes replacement gene clusters derived from a single gene cluster, or may comprise hybrid replacement gene clusters with, e.g., a gene of one cluster replaced by the corresponding gene from another gene cluster. For example, the oxidoreductase of LOL1 may be replaced with the oxidoreductase of LOL2 without an effect on the product structure. Accordingly, these genes may be freely interchangeable in the constructs described herein. Thus, the replacement clusters of the present invention can be derived from any combination of alkaloid gene sets, which ultimately function to produce an identifiable alkaloid.

Expression vectors also include control sequences operably linked to the desired alkaloid coding sequence. Suitable expression systems for use with the present invention include systems, which function in eucaryotic and procaryotic host cells. However, procaryotic systems are preferred, and in particular, systems compatible with *Neotyphodium, Epichloë, Adenocarpus* and *Argyreia mollis* species are of particular interest. Control elements for use in such systems include promoters, optionally containing operator sequences, and ribosome binding sites. Particularly useful promoters include control sequences derived from alkaloid gene clusters. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter, which do not occur in nature also function in bacterial host cells.

Other regulatory sequences may also be desirable which allow for regulation of expression of the replacement gene cluster relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid.

The various subunits of gene clusters of interest can be cloned into one or more recombinant vectors as individual cassettes, with separate control elements, or under the control of, e.g., a single promoter. These subunits can include flanking restriction sites to allow for the easy deletion and insertion of other subunits so that hybrid gene clusters can be generated. The design of such unique restriction sites is known to those of skill in the art and can be accomplished using the techniques described above, such as site-directed mutagenesis and PCR.

Further, the vectors, which collectively encode a replacement gene cluster can be inserted in to one or more host cell, using methods known to those of skill in the art. As such, the present invention also provides host cells which have their naturally occurring gene substantially deleted, transformed with vectors encoding a replacement gene cluster or parts thereof, for the production of active alkaloids. The invention provides for the production of significant quantities of product at an appropriate stage of the growth cycle. The alkaloids so produced can be used as insecticidal and feeding-deterrent agents to protect plants. The ability to recombinantly produce alkaloids also provides a powerful tool for characterizing biosynthetic enzymes and the mechanism of their actions.

More particularly, host cells for the recombinant production of the subject alkaloids can be derived from any organism with the capability of harboring a recombinant gene cluster. Thus, the genetically engineered host cells of the present invention can be derived from either procaryotic or eucaryotic organisms. Preferably, the host may be *E. coli*. However, more preferred host cells are those constructed from the *Neotyphodium* species, among others, will provide convenient host cells for the subject invention.

The above-described host cells are genetically engineered by deleting the naturally occurring loline alkaloid genes or genes encoding tailoring enzymes therefrom, using standard techniques, such as by homologous or heterologous recombination. One or more recombinant vector, collectively encoding a replacement gene cluster of the present invention, is then introduced into a host cell. The vector(s) can include native or hybrid combinations of loline alkaloid gene cluster subunits, or mutants, analogs, or derivatives thereof. Methods for introducing the recombinant vectors of the present invention into suitable host cells are known to those of skill in the art and typically include the use of $CaCl_2$ or other agents, such as divalent cations and DMSO. DNA can also be introduced into bacterial cells by electroporation. Once the genes or gene clusters are expressed, the alkaloid producing colonies can be identified and isolated using known techniques. The produced alkaloids can then be further characterized, e.g. by NMR and mass spectroscopy.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed:

1. An isolated nucleic acid molecule comprising: a nucleotide sequence consisting of or complementary to ORF8 of SEQ ID NO: 15 or a nucleotide sequence encoding a variant which hybridizes under high stringency conditions of 0.1× SSC, 0.1% SDS at 65° C. to ORF8 of SEQ ID NO: 15 and wherein the encoded polypeptide of said variant has γ-type pyridoxal phosphate (PLP) enzyme activity.

2. The isolated nucleic acid of claim 1, wherein nucleotide sequence is ORF8 which encodes lolC in SEQ ID NO: 15.

3. An expression vector comprising the nucleic acid compound of claim 1.

4. An isolated host cell transformed with an expression vector of claim 3.

5. The host cell according to claim 4 wherein the host cell is a bacterium.

6. The host cell according to claim 5 wherein the host cell is *E. coli*.

7. The host cell according to claim 4 wherein the host cell is *Neotyphodium*.

* * * * *

SEQUENCE LISTING

<160> NUMBER OF SEQ ID NOS: 17

<210> SEQ ID NO 1
<211> LENGTH: 23
<212> TYPE: DNA
<213> ORGANISM: Unknown
<220> FEATURE:
<223> OTHER INFORMATION: Artificial primer sequence

<400> SEQUENCE: 1
gttgatctcc aagatccgtg agg                                           23

<210> SEQ ID NO 2
<211> LENGTH: 20
<212> TYPE: DNA
<213> ORGANISM: Unknown
<220> FEATURE:
<223> OTHER INFORMATION: Artificial primer sequence

<400> SEQUENCE: 2
gtttcgtccg agttctcgac                                               20

<210> SEQ ID NO 3
<211> LENGTH: 23
<212> TYPE: DNA
<213> ORGANISM: Unknown
<220> FEATURE:
<223> OTHER INFORMATION: Artificial primer sequence

<400> SEQUENCE: 3

-continued gtctggcgaa ttctacagac acg                                    23

<210> SEQ ID NO 4
<211> LENGTH: 21
<212> TYPE: DNA
<213> ORGANISM: Unknown
<220> FEATURE:
<223> OTHER INFORMATION: Artificial primer sequence

<400> SEQUENCE: 4
gatggccatg tgaggaaaga g                                      21

<210> SEQ ID NO 5
<211> LENGTH: 24
<212> TYPE: DNA
<213> ORGANISM: Unknown
<220> FEATURE:
<223> OTHER INFORMATION: Artificial primer sequence

<400> SEQUENCE: 5
cggtgcgcgt cttctaaact tgac                                   24

<210> SEQ ID NO 6
<211> LENGTH: 25
<212> TYPE: DNA
<213> ORGANISM: Unknown
<220> FEATURE:
<223> OTHER INFORMATION: Artificial primer sequence

<400> SEQUENCE: 6
gaatctttcc gatgcaaggc ttacg                                  25

<210> SEQ ID NO 7
<211> LENGTH: 23
<212> TYPE: DNA
<213> ORGANISM: Unknown
<220> FEATURE:
<223> OTHER INFORMATION: Artificial primer sequence

<400> SEQUENCE: 7
ggtctagtat tacgttgcca ggg                                    23

<210> SEQ ID NO 8
<211> LENGTH: 22
<212> TYPE: DNA
<213> ORGANISM: Unknown
<220> FEATURE:
<223> OTHER INFORMATION: Artificial primer sequence

<400> SEQUENCE: 8
gttgcccacg gtgcgcgtct tc                                     22

<210> SEQ ID NO 9
<211> LENGTH: 20
<212> TYPE: DNA
<213> ORGANISM: Unknown
<220> FEATURE:
<223> OTHER INFORMATION: Artificial primer sequence

<400> SEQUENCE: 9
tggtcaacca gctcagcacc                                        20

<210> SEQ ID NO 10
<211> LENGTH: 20
<212> TYPE: DNA
<213> ORGANISM: Unknown

```
<220> FEATURE:
<223> OTHER INFORMATION: Artificial primer sequence

<400> SEQUENCE: 10
gagaaaatgc gtgagattgt                                                   20

<210> SEQ ID NO 11
<211> LENGTH: 18
<212> TYPE: DNA
<213> ORGANISM: Unknown
<220> FEATURE:
<223> OTHER INFORMATION: Artificial primer sequence

<400> SEQUENCE: 11
tccgagatct ggacgagc                                                     18

<210> SEQ ID NO 12
<211> LENGTH: 20
<212> TYPE: DNA
<213> ORGANISM: Unknown
<220> FEATURE:
<223> OTHER INFORMATION: Artificial primer sequence

<400> SEQUENCE: 12
taatacgact cactataggg                                                   20

<210> SEQ ID NO 13
<211> LENGTH: 17
<212> TYPE: DNA
<213> ORGANISM: Unknown
<220> FEATURE:
<223> OTHER INFORMATION: Artificial primer sequence

<400> SEQUENCE: 13
caggaaacag ctatgac                                                      17

<210> SEQ ID NO 14
<211> LENGTH: 16
<212> TYPE: DNA
<213> ORGANISM: Unknown
<220> FEATURE:
<223> OTHER INFORMATION: Artificial primer sequence

<400> SEQUENCE: 14
gtaaaacgac ggccag                                                       16

<210> SEQ ID NO 15
<211> LENGTH: 25346
<212> TYPE: DNA
<213> ORGANISM: Neotyphodium uncinatum

<400> SEQUENCE: 15
atatttatat taaatagtgc ttattatcta gattaaataa tcctatacta tttatctaat        60
agttttatta ctaatattag ggtatatagc tatactttt cttaaggagt tttactatat       120
taatttcctt tcttacttag gctataacta taatttttag tttagtaagt tacttttatta     180
gattatttat ttaattatag tatttttacta aattaggagc tatctactac cctagactag     240
tgttaaataa aatatttttt ctattctaac taggtaaatt actaaatatt atctaatttc      300
tctaagtagc ttagtaacta ttaaaggtag cttaattaaa tagtgcctat atcttaaagc      360
taaattctac cttatctaaa gtaattttttc ctaagttaaa gaagttagga tccctattct     420
taagctctaa ctatatataa atatatatgt taagtgctat ctaaagctat ttatattata      480
```

```
atactagaat tttctcttaa gtaaaccctt tttaatttat aaagcttaag attaaatact    540
taggaagtgc tttataaata taattagact aggttatagt agttctctat tctattaggt    600
tagccttaga taataaagta taatacttct atagctagta ataggtttcc ttaattattt    660
ttagttatat aaaattaagg tctttaagtt atccctagt gttttctatt taaccctaat    720
tagtaatatt aaactaaagg agtatcttat ccttagactc attttaagtt tataatatag    780
ttagtatttt aactacttat taaagcttta agttaatatc ttacttaagt atcttacact    840
agtttaactt aggtatacct attacctta tctttacttt aaaatcttta ataaagttag    900
taatattatc ccctataaac tactaaatat tgattttta aatttttta ggggttatta    960 gttatagcca atgcatctaa taaaataaga taataataat tactagcaat acctagctag   1020
tataataatt aacttataac taatcttaac tatagtaata aataaaaccc taatagaaac   1080
aagcttaaag gttataaata tagggggggc tataaggtta gattaaagtt tgtaataaac   1140
tttatagcta cgttagcgca agatatagtc atagttcgcg accgcagtca aactcaaatt   1200
cgttcgataa actactaaat attataccta ttttatatag taataaggga tatctaatac   1260
actattattt ctctaagaag cttatataaag gtctttatat taaggcccct aaggggttta   1320
ggtatagtct ttctattatt aggatctttt cctaagtagt ttttaaatta ggtttatact   1380
aaactagtaa ctattttaga attaattaat ttctaactag gaactagagt actaggtaat   1440
agaaattctt agagatcctt taggtaactt agctacttac taggccttac tttacttagt   1500
tatttaaaat aaaataaggt aaggttaaat atagaattag ctaagagtgc ttttaattaa   1560
tctattagaa aagtaatagc ttaactaaat atctaaatac ttataagact ttactaaaaa   1620 agggtttta gtagtgtaat atttatagtt ataagtaagc tataagtaaa ggctattgat   1680 ttttaaat tttttggggg ttattagtta tagctaatgc atctaataaa ataagataac   1740
tataattact agtaatacct agctagtata ataattaact tataactaat cttaactata   1800
gtaataaata aaaccctaat agaaataagc tttaaggtta taaatatagg ggggctata   1860 aggttagatt aaagtttgta ataaagttg tggctgcgtt agcgcaagat atagtcatag   1920
tttgcgaccg tagttaaact caaattcgtt cgagtttta agtaaaggct ataagtataa   1980
ttatatagct cttataata agctataaga ttctaatact tagctaaata actataaaat   2040
taataataag tcttaagatt aaatagttta taacactagg tagcgcttcc tatcttaggt   2100
tcttatattt agagatctct agtaagggggt taatagctta gctagtgttt atagaatata   2160
ccttaggatt agttactatc ttcctctata gttttatata atataatttc ctcttcttaa   2220
tctatcttaa ctctctaagc ctagctagcc ttatattaat actatagcct cctttaggta   2280
taagcctagg ctattaattt atattatact atagggaaaa taaaataaag gggttttata   2340
taaaatagct tagtaatagc taaagaattt agctagaaat acccttctaa ttaatcttag   2400
ctagaagtaa gttaattaga gagtctaagg tccttagggt tttaaaacct atttctctac   2460 tagtttatt aagtaaaaaa taatacccta aaagacataa tactagccta agttataggg   2520
tagtaatagc atttacttac actaaagggg ttaattaact taatagtagc aattataata   2580
atagctaaat ctatctctat atatagggat agattagatt agattaaata atctattaga   2640
ttagaaatgc cttttaatt aaatcagggg aaaatagtct tattaattta tcttattaaa   2700
gtaaatataa tagtagctat agtaacacta ggccttaaag tcaaaaatct agagttagtt   2760
atatataatt tatactaaag aaatctagct ataggtagtc cctttataga ttaaataatc   2820
cccttatcta gataactaat atcgttatcc cttaatgtgt tatccattcc tttaatccct   2880
```

-continued

```
agtgcttatc atcacgatcg cgtgttttgt gggcgcgcgt atcatagcac acagtacttc   2940
ttctagattt ggactaacgt ggtatgcgca tttagtggcc ctaggacgta tggtgccgga   3000
ctgttgtagg ctatccgtcc tagcctaacc tatctaggca ttggtctagc aacaggctta   3060
cgggggctag ctaagatgta gatatgtaca agatgctatc aaactgctat tgtgtttgcc   3120
gagaaggtta ctagcagatg ccaccgacgg aaacgatgcc catttcttc tggcacagaa    3180
tcagagacgt attgggtgtt tgtcaatacc agagtctgat cagtggaaca tggaaaatcg   3240
gggggacaaa atctgcctag ccgtcatcca aaaaaaaaa aaccaattgc tacttgcgtc    3300
tagacctgaa gagtgtatcg actcgatata cgacagaaag tggcttcaca gaagacccgt   3360
ctcctctaca tgccacgctt gaaacccctc caggttgttg ccagacagt tttccagctc    3420
ccgacgatac agaatcaacc ccccaaccct gatcagtttg ttagagcagt ccacagaaca   3480
aagcgacaag agcccttgtg caacctacca agttttctct tccttgttag cctcagctgt   3540
tttcttgctt ttgcgtgcat gtgtatggta gagtgtcttg tcccaaagta ggctcatctt   3600
cctctcccac tggcagtggg atttggaagt cgcctcgagt tgacaaatgc cgcctgttg    3660
gcaccttgcg atgatttcgc acaaccactc tacctgaacg gtgatgaccg cggggagtt    3720
gaccagaagt gtagggcact ggggtccata gaggatgacc atgttgggga atgaatgaat   3780
ggccattccg agatgcgact cgacaccatc ggaccaggca tcttctaaac ggatgccatt   3840
ccggcctctg atatgaagac tcctgagccc gcttgcctcg tcgccaaacc cggtggcaag   3900
aattatggct tcgcattcaa ctgtctgccc atgaacgcgg atacctgtct ctgtaattaa   3960
ctcgatttgc tggttgctga tgtcaataac cttcacatgg ggttggtcca taacctcgta   4020
aagatcctct tccaaacagg gtcgcttgat accaaaggca aaagatggaa tttgaggcac   4080
caggagctcc cgtttggcca catcgctgat tctagctcgc gtccgccgag cccagaaatc   4140
atacgcatcc cggttggctt ggatgttctg gcacagatcc cggaacccag ccatccagaa   4200
agcccagcct cccgccagat agcgttgttg ataaaaatgg tttcgctcct ctattgggac   4260
atccaacgtg tcctggtcac ggggcacgta gccgaaaccg tttgaagtct gcagtccaag   4320
tcgtagggct tctctgtggt cgtcgggtct catgcaaagt gccgttgccg tctggctcgg   4380
gctgccgtat ttgcgtagag tgaggcatgg agactgctgg aatatcgtca tggccttggc   4440
tatcttaccc acagattgga tgatctgaac tccgcttggc cccgttccaa tgacagccac   4500
cctcttaccg cgcatactga cagcgtcatg aggccatttt gcggtgtggt agatgggacc   4560
gcggaatcga gacattcctg gaatcctggg gatgttgaga acggacgaaa accctacagc   4620
tggaatgaac catcgcgcct cggctcttct gccatcttct aaagagacgg tccatctctg   4680
ggtagtttct gagtaccggg ccgcggaaac cgaaacgcca aactcaaaac tagcagagat   4740
ttcccatcgc ttgtccacgt ggtcaaaata tctcagcatc tctgcacggg tgggaaattg   4800
ctctacccat tcccaatctt ggagaagctc cgcatcatag aactggtaga agggaaacag   4860
gctgtcgact gctgctcccg gataagcgtt ctcgcgccag acacctccaa gacgttcctg   4920
gcgctcaaac ccttggactc gaaatccgag ctttcgtagt ctttagtcat agttcagtcc   4980
tacctctcta ctctattcgt gtcttggatg caacgtaga ctctcacctg tagacagcga    5040
gaatacctga aaaccagcg ccaacgacga ttacgtccaa attggtcaat gtcatcttag    5100
tgaaatgaag aagaattaaa taatcatatg cagaatagaa gcaaattttg gtgtatcaga   5160
aatgtcatca aaggctaaca gctccgggga cagaaaagct tgatcgaggc tgcaatttac   5220
```

-continued

```
tgagaggcgt aagggactga tactaagacg gtcgattatc tgtgtgcgag tggtcagaat    5280
gggtaactgc gcatttggat agcccagttt gggaggggga gtatagtcgt acacatggat    5340
tcgcaatttg ggaatgaagc gttaagtctg ttatggtata atagggtcac taaatgcaca    5400
taacgcgtta gtcctaatcc ggattaacga tccatgcacc ttatgcctat atgtgtcata    5460
tttaaaggta ttgatattat taaagctatt acaattacca ctatactagt attaacttaa    5520
gtaattaact ctctattata tacgccttaa ataattacta ctaaataaat tcaaccacta    5580
taaatccgtt acttactaag tattaatagc actgattata tcttttatag ttatatacaa    5640
tatctttatc tttaataatg acataataaa gggcacttaa aaagagcctt attatattat    5700
attgcgttgc attgcattgc gttacattat attagaaggc ttttacaat aagcattata     5760
gtaagccact tgcattttat actagctctc taatatactt agcaagggat taagtaaaca    5820
tgtactttt ttgttttagg actaacgcgg tatgcgcatt tagtgacccg gtataatagg     5880
gcataggaga ggcgtgagtg gggtgttcac tcactccgtg tcacgtcact tctcacaaag    5940
gagagggagc gtggctattc ggacctgcgt tttcttgctt actagagctg tgcctaccac    6000
gtaatagggc cacatcccac atcccacgcc ccgccactaa attatttgta tagcactccc    6060
tagcaataaa aatagtcaga attacagtac acccctgagt tattttacag atctacataa    6120
caggggggat tgagcgaatt aagtgctagc aaagaaataa gggagatagg ggctaggatt    6180
agcaagtacc tagattcctt tatactttat atagaaaatt atatatcttt tagtagtgct    6240
atatatgcta tatattttcc ttatagctct ctaaaataat ataggggttc tagtgcactt    6300
atagctaatt atagctatta gagaggaacg aaaaactagg gcatgtagat ttgtaaaatg    6360
aatgtgtaca ggcctgtcgg ccccgcccgc cgcaataggc aatagctgta ctacgcccgt    6420
agtggccacc cacttatcat gccacgcccc acttcttttg gttcgcgtgc cacttcagtg    6480
gttattactc cgtattcata agcttgacaa acacacatcc gcgacaacgg tatcctcatc    6540
tgcagggccg cataccataa tgcttgctgc agctcattga taatatacct ggcctaagat    6600
agacacgacc gaccggctgg agtcatcggc tttgcctggc cctccgctat tttgagagac    6660
aagatcggcc tggtgactac aatttgctac caagacagat tcgctgaata tccgcaagca    6720
agcaagctgc atcatcaaaa cataaataac gaccaaagaa tacacggagt agaagaaagg    6780
aaggaccaga acaagttggc gattttccaa cttggttact cacccaagcc gtcactctgt    6840
tcatatcatt actcgccttc cagtgtcttg cccaccttgt ttcaatattg tcgtcgagca    6900
aaatgacagt agatacgatt acttcgactt ctaacgggaa ccaagatgtt ccaaaggagt    6960
tcttcccaaa agaattcgaa actcagcttc tccatgttgg gtaggttatc gcgcctcata    7020
tgacggtcct ctatcccaga actaatcagt ttgcgattca agccggttcc cggacatttt    7080
aggcagttgc gcggtgcctg tatacagttc ggcagtaaga tcaagccacc gcctcctcga    7140
aacccaccaa ctatgccaca tgtactgaat tcttttccct ttttgcgcat cttgataggc    7200
ctttgagttc aacagcgttg cccacggtgc gcgtcttcta aacttgacgc agttcggcaa    7260
catctacagc cgcttcacca atgtttgtct ctttctcctt ctccctcatg actgcttttt    7320
taacgaggac acaagctaat aaaacaaaac catccttcaa cagcccaccg tcaatgtatt    7380
gcaaaatcga ctggccgggc tggaaggagg cgtcgctgct tgtgccgtcg catccggctc    7440
tgcggcggta gtcgtgacgg taatggccct cgcaggcgtt ggcgacaact tcgtctcatc    7500
cttttcacgtt catgctggca ctttccacca gttcgagagt ttagccaagc agatgggcat    7560
cgagtgccgc tttgtgaagt ctcgagaccc tgcagacttt gcggcggcca tcgacgacaa    7620
```

```
gaccaagttc gtctggcttg agaccatcag caaccctggc aacgtaatac tagaccttga   7680
ggcagtctcg atggtctgcc acaccaaggg cattcctttg attgttagta tcccaatgaa   7740
aactgtccgt cccatagggg gggttggggc taaaattcgg ggggatgtgg ttcccatcca   7800 agatttagt gcgataacac ctttggctgt gccgggtact tttgtcgtcc catcaaccac   7860
ggcgtcgata tcgtcgttca ctcggccacc aagtggatcg gcggccacgg cactacggta   7920
ggcggtgtca tcgtcgacgg cggtaccttt gactggggcc agcacccgga tcggttcccc   7980
cagttccatg atccacggac gcgactctgg gaacgctttt cccgtcgggc gtttgctgtc   8040
cgctgccagt ttgagatcct gcgcgatacg gggagcaccc tcagcgctcc tgcggcccag   8100
cagctgctgg ttggcctcga atcccttgcc gtgcgctgcg agcgccacgc gcagaatgcg   8160
gccaagattg ccgactggct gcgtgagcat cccctcgtgg cctgggtcag ctatgttggt   8220
cacccgaacc accccgatca ccagggagcg ctcaagtacc tcaagcgagg ctttggctcg   8280
gtcatctgct ttggtctacg ggggggtttt cgaagcaggt gccctgttct gcgatgcgtt   8340
gaagatggtc atcaccacta ccaagtgcgt aattaaacta gccccttctt ctcccgagag   8400
agcatcgttc tgccattcta acctcgcttt gcagcctggg ggatgccaag accctgatcc   8460
tccatcccgc ctcgactact catgagcact tcagttccga gcatcgagct gaggctggcg   8520
tcacagatga tatgatcagg ctgtctgtgg gtattgagca gatcaaggat atcaaggccg   8580
acttcgagca ggcctttgag caagtgcttc ggggtaagaa gagtcttcgt aagccttgca   8640
tcggaaagat tctcttgcag gatgagatca atgaagactt atttggacct tcagcttgtc   8700
gtgacgtaaa taggggtcat tgcgaggcat ggtaaatgtt ctaccagaag tggcatggaa   8760
gtattttcca atagacctgt aattcacggt tgctacgttt tttcatactt accatgcgga   8820
tttattttga taatatttct ttaagtgtgc agaactcgta gtcacttaca aagctaattg   8880
ccgtaattaa tctttagtgc gccatgtcct cttgactatc ttgtaaacga aggggcatta   8940
ggcgtgcttt gctttgtctc tcctcgtgtt tttaagtttt gctatattaa cttgaatatt   9000
attactaact agatgctagg cttttttacta tttacaaaca cctgtaacaa tcagcgcggc   9060
gttaggcaac tgcagagatt attttactat agtatagact ataatgccat actttaatta   9120
atcttcagta cgctatgttt ttttcactat cttgtacaga ttaaacaaag gccattagg   9180 catgtgttgg gagcataaag gcaaagaggt cagagacagg acaaccgtat agtgaatcct   9240
tggatgacta agcgtagttg cctagctagt agatctcctt aagcgtgcta cagcttgtca   9300
agtcacgtta gctagagtct atatctaatt agataaaagt acattaaaat agtatatata   9360
tttatatgta aattagctaa taatcgttat actagtaatt ttctatagta tagattacta   9420
tattacactc attaattatc ttagataagt agtacgtact tacgcggtta ttaaccttat   9480 agcaggggg gctgacgtaa ggtagcttag gagtataagg gggctgtaag ggataatcct   9540
ttcttctctc ctccagtttc ttaatactac atcgacgccc tatcgcagtc gcctaggggc   9600
tagtctataa caggaggtta gagtttgaga catttacgca caaacctaat ataggtagcc   9660
ttgttattag taacaaagaa tcttagctat tactcggttt taacaaacca ggccattagc   9720
cacggcagca tgctccactt agtctctccc agtgttttag agttatacta tgttattaca   9780
taaaatacat atactattat tttaaagtaa actttcacat tttaaaactt attatgttaa   9840
aagtggataa ttcatgcata tattaacttg aatactatta cttactactc gatactaggc   9900
tttttactat ttacaaacac ccataatagg cggcgtggcg tgaggcaatt gaggagacag   9960
```

| | |
|---|---|
| tctcacaata gcagggagca tatcacattc atttatagta cagatgccga gccaaatgcc | 10020 |
| gtgcgtgatc gaaacggtga gccaaagcgc agcacaccat caagatgcgg ctgtaatctc | 10080 |
| ggttgtcact tggaagcact tggaagcact cgtgcataac gcaagtcgct ctctcataca | 10140 |
| tggctttcag agtttatgag ggactagaac agacaagtct ggcttttga caaggaagta | 10200 |
| gctggacaag gttcgcaggc gctctgaccg agcataaacc aatattggag actggagact | 10260 |
| ctgccatgtc ttcaataggc ccttatgtag ccttgcttgt gtgtgtactt gcagggatgt | 10320 |
| ttataaatat gtgtatgttc gagtatcttg ttcggttttg taaactcaaa ctcgccagct | 10380 |
| ctcagcctgt cagccgagtg aattgctatt gccattgtat tactccagaa cacgtatctt | 10440 |
| gcacaaactc caatctcagc aatggccacc gtcgtacgag aagcatttga gaaccatgtc | 10500 |
| aagctggtcg agagtcggaa ctcgcccggc catgtgcttg cttcttctga ggcctccttc | 10560 |
| tttgttgccg acttgaacga cattgttcgt aagtgggcgg cgtggaagaa agctctcccg | 10620 |
| gatgtcaccc cttttttgg tacgtcctca attcccccca tttcatgtct cactaagctg | 10680 |
| ggaagtcccg tccgagggtc cgaatcaatt gacttggagg cagccgtgaa agcagctac | 10740 |
| gatcgacggt tgatccagac tctggccacc tgtggagccg gatttgactg tgcctcggtg | 10800 |
| gaggagattg agttgatcct ctccttgggc attggcgcag aacgaatcgt cttcactcat | 10860 |
| ccgtgcaagc ccgtctctcc tcgggctttg ccgcaagctt gggatcacgc tcatcacttt | 10920 |
| tgacacgaat gcgaagctcg taagctcacc atcactatcc cgaggctcag accgtcctcc | 10980 |
| gcgtcttcgc cgacgaccca accaatgccg atcctttggg taccaagttt ggcgccgcgc | 11040 |
| gggaggacat tgatggactc gtgcgtctgg tcaaggagtt gaacatgaag ctggccggcg | 11100 |
| ccagctttca tgcaggtgcg tctcgctctc ggtacctcgg ccggtgaaat gcatgcagct | 11160 |
| cgctaacggc ggcaattcca cgccctgttc tagcccctag cgtcgctgtc gacgcagctg | 11220 |
| catacgtgcg gggcatccgg gacgcagccg aggtcttcgc gcgggcccga cgggtcgggt | 11280 |
| tgaaccctac ggtgctggat attggcggcg gctacacaga ctcgacgttt caacagattg | 11340 |
| caggggcggt caggccggcc atcgccgagt gcttcaagtc gcaagtggtc gagggacgcc | 11400 |
| ttcgcatcct tgcggagccg gggactctct tctcctgcag cccgttctat ctagcagtca | 11460 |
| aggttgtcgc gcggaggagg aacgccgctg cgtttgggaa tgagccagcc acgcgtctct | 11520 |
| acatcaacga cggcatctac agcaacttca tgatgcgttt catcgtcaac atgacctcct | 11580 |
| cgcccgtggc cgtcatccgg aaggggGtgt ggtacgatca gacggagcaa acgatgcgcc | 11640 |
| gcgaggcgtg ctctctttgg ggccggagct gtgactccaa cgactgcatc aacagggatt | 11700 |
| gccggctcga tccggaagtg ggggtcgggg actggcttgt cttcaaagac atgggtggtg | 11760 |
| agcgtctcaa cttttcccc cttttccttt tcgtttttgg gtccctgtgg agaatagcat | 11820 |
| atgtaggagc taaccatgca tggtgggcag cctacacaac ggtatgtaac accaccttca | 11880 |
| atggcttcac cagttccaat cacacaatct acattgaacc cacccaagtc gacaaagccc | 11940 |
| agtcgacctt tgaacagttg gagttggcca tctgagtgcc agttcgggga gacccacacg | 12000 |
| cggcacgtgc cgtcccgggt tcccgggcgt ggctgcatga cgctagacgc gctagtctag | 12060 |
| tacctactcc gttccgtact gtccttgcag cagtccgtag tcacaacaga tggcttggat | 12120 |
| caattgatgc acactccctg attagcttgt ttgacacatt ccatttggct tcgtgcacat | 12180 |
| catgatacaa ccagtacatg tttcctccag tccttttgta catggccacg ccgagctctt | 12240 |
| gtaagtacct cgtcgagctt ggtcttcctg caccaagtta tgtacagtgg gggtgcagat | 12300 |
| gtaaggtgca gatgtaagga taaccacaaa aattagtcct gttaggcaaa atgacccttat | 12360 |

```
aatttaaata aatagctaaa taaaatatat aatatataat tatactaaga agttatttct   12420
cttttaccta tattacttaa aactttatat taaaccctttt agcgtgtgaa ataaattaag   12480
ttaaacctaa gataaaatcc ttcattatcc tcacatctgc accccactc taggtgccgc    12540 gctcccggag aaggggtcca ccccaagtca ccccgagaac ggtaaaaatg acgacatatg   12600
gcggaacccc cttctcttag cgacaatcgc aatgagacgg acaaggtaca acgacctgag   12660
tttctgaccg actggcataa gtgctcatga ttgaatacta ggtagcagac tgtacggact   12720
tagttcgttg tttcagtgca aatcacttca ctactacaag cctcaggcct ccgtcgcctc   12780
ctacatgacc gttgctgctg tcttgcgctc atactcaaga gcaactcggc gggccagcca   12840
ctgccctgcc gtcatccggt ccttccactc gagcgtgctc cactttcctt gcttctcgca   12900
gccaggcaga ggttcgatca tctcgtccag attcaagtgt ccgaagaaga cgagcgagta   12960
gcgctgcacc agctcgtcat cgtcaccggc acttccttcg tacatgtacc ggctcggcgc   13020
cgtgacgcgg tggagggcgc tccgccatct gccgttggtc tgcttctcaa gcaggtcccc   13080
aacttgaaca atcatagccc ccttgatcgg aggcacaggt cggtaaatgt cttcctcgta   13140
gtcgtgcagc tcaagccccc cgaccatgtc ctggaagagc atggtgaact ggcagtagtc   13200
cgtatgcgcg ttgagccggt tcgcggatcc gctggccagc tgtgaaacgg gctgccccag   13260
gaagtagttc caagttgagt gggtgctcat gtggcgcggc tcaaacttttt ttccaatgta   13320 atccagatcc tccatcccga ggatttcgca cacgagccgc atgttctgga gagattgctt   13380
gtagcaggcc gcgaaccact tcttcaagaa gtcgagaaag cccggagat gctgctccac    13440 caagtttaga tcggggcgc ccggggggta cgttccgcaa gggtcctgca gctccatggc    13500
ctctttgagc tccgtcggcg tctccttgcg gagcctctcg atctcgtcgg gatcccagac   13560
gccctgcgag gagatggcct cgcctgtgcc cgtccagccc tggaaatgct ttgatacgtc   13620
aggtgggatg tgaaccgagt tcttgaccgc cagaggcagg tcaaaaaact tcttgcactg   13680
catttcaaaa ggcacacaag atcaattagc gatcctaact tgcatgggga atgccagccc   13740
attcttgagt aaccaggcca gctacttacc caggcgaatg cttcctcgag cgtcctagtt   13800
ccaatactgt ggttaataac gtagatggct ccgtgatggc tccatgcctc gtcgagctgt   13860
cgcaagtatt tcttgcgctc attcccgaca ctggcatgga ttgcctcaaa gtccatcact   13920
ggcacattag caggcttaac aggcttgttt gttaccgtca tcttgggagt tgaacagata   13980
gaatcttgat gttgaatttg ggattagtgc ctcggaaaga gtgaggaatc gtgatatgtg   14040
gagcggatcg ttaaataaag gctttgagga ggtcatttat aatagtgtca acaagctgat   14100
ttatcacact gcaatcctgc atctatatga cacggtctct attattggag gggtctctta   14160
atgcgcatac cgcattagtc ctggaacaaa aggagtacct ttccacttaa tcccttacta   14220
aatatactag ccatctttag tagtgaatat aagtggctta atataatgct tatagcctct   14280
tctatagaaa attgctttct ttttactatt atcaaagcct tataatataa cgtaatataa   14340
cgcaataacg taacgtaacg caatgtaacg caatataacg taatgcaata aggctctttt   14400
taaatactcc ttattatatt attctttaag atagctattg tatataacta tagaaaattg   14460
aattcatatt attaatactt agtaagtcag tgagggtta atagcaaaat aaattcataa    14520
taattcttca aggtatatat aataaagact taattattta atttaatact agtatagtag   14580
taattataat agctttaata atattaatac ctttaatat cttatatgta agcatcttcg    14640
ttaatagtca aaatcaatag acgcaagcca cactaaagtt aggtgtgtag gactaacgct   14700
```

```
atatgcgcat ttagtgacct taatcaacgg tttcaaagtg gtatgatctc attagattct    14760
cggggatcct cttgagggac acgatacaaa tcttcttgag ctacgtttgc catcgttatg    14820
agaagtggct gacaagtact tcgtaattta agagcatcgc gtctggcgaa ttctacagac    14880
acggaacgtc agtgacacca aacccattca gcccacccac aaaatctcaa ttcgactgta    14940
ttttctaacg atgctcgatg aaagcccaat gaggaagggt gattctgtga gcaacgacca    15000
aagcaacccg gagagcaatg catctgtttc aatccatcag cagaatcaaa tcatcacctg    15060
tgtctcccca ggcccagtct gccccaatgc gatagaaatc aagcgtgaca ttgtgatcgt    15120
gagactacgc cccgtcgaaa gttgtccagg ctatcgcttc tttcgccgag tctttgagac    15180
actagagaaa tggcagctgc aagtcgacat gttctcaacc agtctggggc gaataacctt    15240
ggcgctgggg gccgcagcgc tgcaagccgg cattagtgac tcatgcagtg ccagaaatga    15300
catgatgagc cgggatctca tgcacggcat gcagaagcta ctcccggacg atcacataga    15360
gctctttcct cacatggcca tcatctcggt cgttggacac ccgagccgac gaatggccgg    15420
ccacatcttc gccaccatgg atgccaatga tattcccacg gtcatgattt cgcacggtat    15480
ggcctcaatc ctttcccgtt tccatagcaa atcatcgtcc cattcttctg accagcatgt    15540
tcagacgccg ccaggctcgg tatagcctgt gccatctcgg agcagtacac tgctaaagcc    15600
ttgtgcgtct tcgagcaatg cttattccgg tactccttga cacattgaac cgttatctca    15660
gtctcttcat caaaactctt ctcgttgcag aattagatag attagatgca caagacactc    15720
gttgtgggct atggtttttt tgccgtgata gacagctaaa actaaaacct cattgtagtt    15780
acaagcagct ttagtacttc ccgtgatact gacttttctt tagcagctga tcgaccactc    15840
tagtgacaac aacgttcaag attccttcgg atctagtgct tctgaagact aacttccacc    15900
gagtcctagc tcctggagaa gactgtcgcg caccatctcc atgacgggag ccagaaagtc    15960
ttccgtatag tatgcatcat tgtagtacaa gtacagccgc atagtgccgc ggaaggtaaa    16020
tagctggaac tcgatggttg gatcagtcgt tgcattgacg agggctacgt cttcgatctc    16080
acaaacaggg gcttgtgccc ccttttttcc gtacgcgcgc gctagatatc tctccaacac    16140
gccgaggcta ctgaggttgg gtacccggaa gggcggacag ccggcaacgg gcaaggagcc    16200
aaggaaagcg gcctcccggc tttcatacag cggcagcagc tcgagaaagc tcacagggtc    16260
gcctgccggg tctgagggca gcgccgacag atctcgcgag taaacagcac ccagacgttg    16320
cgtgaggtcc tcgaagccac ccgtgagaca gaacggcacg acaaagatac agaggccgag    16380
tgcgtagtcc ggaacaaccc acttggggtc cagaagtgga cgcaggttcg cgacgagggg    16440
aatgagcatg ttgcgcgctc cggtgtgctg ttgttgaggg aatgaggccc agacgcggac    16500
aatactcgcg tggacggcgg ccgagacgct cacgcccagc ttcttgcaac ccgccacgat    16560
ggcctcgagc gtcggctcgt cgaacaaagt caccaggtgt tgggtgttgg caggcgcggc    16620
gtcctcggac ccctcacgca cggggagaga caagctgtac aaaccatgat gccaatgccg    16680
catcagctca tcgacggcac gctccacgcg gtgtgggacg ggtgtctcct gcggcgggaa    16740
ccccagaata tagtcgatgc cggggcgggag ggacggttgt ttgacatcgg tagtgtagca    16800
atctaggttg gcgtcgaggc cgagacggaa gactgactcg agaccgagca tgaaggtgtt    16860
tgtcgccttg tatattccca cagcgtcaaa tcggaggtga gtgctgcgaa taatcaaggt    16920
cgacgaagga ggaaaccagt aggccattgc cgttggacga ggttgaaaga tctttccggc    16980
atcgtccacg tccctgaaaa cagcctgggt cccttggttt actgtggaaa cttagccgca    17040
gccactcctc aggatccatg aggggaaccg taaccaggta ccgccctgtc tcatctcgtt    17100
```

-continued

```
ctgaataggg cggatatatt gcgcctatga gcggctggac atatcgaaaa acaagccaag    17160
cgcggcggag gtaggggatg gggtcatcaa tgtcttgggg cagtcgtaat ttgagcttgt    17220
aggtgagacc ctcggcttca cgaccaggag gcgtgttggc gcgttggata cgggcaagca    17280
gccagttctc caccaagtcg aggggccgtg tgagagagcc gtcttctgat ctggtccatc    17340
cgggagcgac aatggcatga ttccctgggc tggccatggc tgctctgcct gttaagaaca    17400
gcggggatag tctgggagag taaagcagtg agggctattg gatattgacg acgaaaacct    17460
tgcaatgtaa gaagtaagtt tcaaaccagc accataggca agcctcctat ttgggcgact    17520
ttaccgaatt tactactata tcttagggac atctaaatgc gctaccgcgt tttttgaatg    17580
cgctaccgcg ttagtcctaa aacagaagaa gtacctttttt acctaattac ttactaaata    17640
tactagccct ttttagtaat aaatgctagt agcttactgc aatatgcaat gcttatctcc    17700
ttaagcgtgc taaagcttgt gggtctataa gccctgcaaa ttgtatatat ctcttgttta    17760
cttttatcta attagatata tatagaccct agttaacgtg actccacaag ctttagcacg    17820
ctttaggaga taacctttcc ttttcttcct tttattatt ataaagtctt ataacgtaac    17880
gtagcgtaat gtaatgtaac gtaataaggc tttaaatatc gcataaatag gcatcttaat    17940
taacagcgaa aatttacaga tgtaagctac actaaaatta ggtgtgggga ctgtctttcc    18000
gttttaggac taacgtggta tgcgcattta aaaaacgcgg tatacgcatt tagaggtcta    18060
atttcgaacg ttttttcatta tctccttgga ctctgtccac cttgtgagtt agtggggccc    18120
ccacaggccc cctgctataa ggttagtaac cacgtaagca cacgaacgta tagtgtagta    18180
atttatatag ggaaaattag tagtatattt actattagct tatttatata taagcaaata    18240 taccttaat ccacttctac ctaattggat atagacccta gtaaacgtga ctccacaagg    18300
tagacagagt ccaaggagat accaatctac ccctaccttg acaactataa atcccttact    18360
tacttataag atattaaaag tattaatttt gttatttatg gttatataaa atagctatat    18420
cttaaagaat aatataataa agggcattaa aaaagagtct tattgcataa tgttacattg    18480
cattgcgtta tatttgtgat aatctaggct ttggctagac ttagtaatat agttgttgat    18540
tgcgtaattt aaagggactt gtttcacgcg tatccttttg ctatggtgca attggattag    18600
gcacatcacc cgtacacgtg ctcgcagaca tccgcgatag cccctcaggc tacaccgtaa    18660
taaaattgca ttatattgcg ttacattgcg ttgtgttgcg ttgcgttata ttataaggct    18720
ttttataata ataaaaagga aggaactctt ctattgaaaa attgataggt attatagtaa    18780
gccacttata tttactactc ataagagcta gtatattcag taagggtta ggtaaaaata    18840 tgtacttctt ttctcctagg actaacgcgg tatgcgcatt taataaccct aagccaatta    18900
taaacacatg tcctgacttcg cattcgtcat tttcggcggg gaatcatcag agcacacttg    18960
cctcatcgtg gtgggtttga tggccaaaag gaattcggat atcagccttg cccgcagcgt    19020
ccgtgccgcg cggggagtct tgctctctct ttgggtctgt ccaatgtccg gcgacctgat    19080
catatgatca taatcacaca cggagcaccc ataacctggg gtcaatatat aagtcagccc    19140
atgtgttctc aaagggcttt tctagtgtcc ccatcgccgg ggacttgatc tcgtagcaca    19200
cgcaccatcc cacccattgc cgccgacggt tcatacacaa cttgatggat ctgacccagt    19260
tcaacacagc gggcatcgtt tggccgacgg ttgctgccat cgccatctcc tatatcctgc    19320
tgtcgagctt tctctcttgg tataggctac ggcacatccc cggcccttc ttggcctcga    19380 tctcaagtct ttggaatgtt ctaaacatcg tgactgggcg cacgtcgcca gtgctcgaga    19440
```

```
aactgccagg aaagtacggc cgctggtgc gaaccggccc caactacgtt ctcacagatg    19500
atgccgaaat tttacgtcac gtcaatggcg ctccagcaca taccccgta atgggtgtaa    19560 gtctgtccat atcacatgtc ttttgaaatg tagggagact cagagaccca ctcacactgt    19620
ggcttccagg gtatgaaggc ttcaaggtcg atgaacacga ccatatgggg tcccatatcg    19680
acacgtcggt acatgacgcc atcaaaagca aggtgattgg ggggtacaac ggcaaggatg    19740
ggatagacct cgagggggcc atcggatcgc aggtcaagac cctggtcagt gagatccggc    19800
gccgtcacct tgggcaacct gtcgacttct ctcgtctgat gcgtcagatg gcgctcgacg    19860
ccatcaccgc cgtagccttt ggcgaggccc ttgggttcct gacggccgaa gacggagacg    19920
tgttcggcta cgtcagcgcc gttgacaaga tgctgaccta cctgacactt gccagcgacc    19980
tgcccgtagt gcgcagcgtt gtccggtcac gccgcatggc gccggcggtg cgttgcgtcc    20040
tggcctatac tggcattggc cgcatgctca accatacacg ccgggtggtg gcggagcgct    20100
acgcggccga cgaccccggg aagggcgaca tgacggcctc attcatccgc aagggctca    20160 cgcagatcga gtgcgagggc gagagccacc tgcagctcat cgccggcgcc gacactgccg    20220
tcacggtgct gcagctccac gctgctgtac atcatgacga cgccgcgcgt gtacacgcgg    20280
ctcaaggccg agatcaaggc cgcggtggat gccggcgagg tggtcgaggt catcaccatg    20340
gcccaggccc agaggctgcc gtatctgcag gctgtcgtgc tcgagggctt ccgcatgcgc    20400
ccggccgtcg tgtacgggca cttcaagtcg gtgccggccg gcggcgatac gctgccgaat    20460
ggtgtacgcc tgcctgcagg caccgccatc gcccccaact acatagcact gacccggcgc    20520
gccgacgtct atggcgccga tgtcgatttg tttcggcccg agcgtttcct cgacgccgag    20580
ccggccaagc gccacgagat ggagcgcgcc atggacctga acttcgggct ggccgctgg    20640 cagtgcgctg gcaggaacat tgctctcatg gagatgaaca aggttttctt cgaggtcggt    20700
ggatgtgcat ctccgctctt tgcttttgtt tcttttcctg ctattactct cgccctcctt    20760
tgctatcctg acgcgggcga ggtatgagac gagatgagag actgattcaa tgcgcagtta    20820
ttacgccact tcgacctcca gatcttgtat ccgggcaaag catgggatga atacacgtaa    20880
ggccttctga aaccttttt aatacctttc gcgcataggc gtctcgggtg gcgtgagcag    20940
cgtgccatgg atattggagt gctaaccagg ttacctctta cctctgcagg ggctgtggta    21000
tattcgcagc ataacatgtg ggtacaaatc accgagagct cgtgagagag cgcaaaggtg    21060
agtatagtgt acagggatac acatggcagg ggtggctacg aacgtccatg accacgtacg    21120
aggcggtacc gatgggcggg aaaggacacg actgagacgc ctggagagaa cgatgaagat    21180
ggggtaagga attatagcaa tcagaataac gatcgtgttt gtgcgcgtcg ggctttgcct    21240
cgcactgcct acctaaacaa gtcccgaagt gatgaataaa attcggcctc ggtgccttcc    21300
catttgctct gagccaccaa tgaagaatca acttggttag aaaccctcct cgccaagacc    21360
atattactag ctgtgataag caccacctgc aaatgctgta ggcagcttgt tatttaaaag    21420
gccgacaaac cgcagcatct ttggttagct gggatttagt ggtgccacct atatgagtcc    21480
gcaatctatt gtcccatctc cctgttgagt atctcttcgc atattacctt gagagaattg    21540
ccggccatct caaaatcact gacctccaag tatacttgcg cacagagtct agcccatatc    21600
catccgcggt aatcgatgat gggtatccag gtcttgtatc tttccgccag agcctttgtc    21660
aagtaacgaa ctgccgggcc gacctctttc tccgtcagag cgccgcccgg cacatgagct    21720
ggggcagtgg acgggcccgt ggcaatggcc aagggaagtc gcactgtcac gatgccgcag    21780
tttctcatct ggccatctac cccggcccca agaccaggct cctccaagac ctctgtctga    21840
```

```
agaatatcgg cgatcttgtc accaccctct ttcgcgagcc actttatgta ctcgtaaatt   21900
gccgcctcgc caccacagac gtctcgcctg aagcggaggg cggccgggat gcacagatgg   21960
ggcatgtaat cgctcgtggc agtgtaggcg aacagtgtct caaacgaaga cgccgtttcg   22020
ctggcactga ccatctgcga ccacagggga agtcgagagt tgccattctt gggaataaat   22080
ccgaaagagg tcgggatgac ggagcgcatc atgtgctggt tgcgctcggc aacgtatagg   22140
acagcacaag gtcgaggaac aaataaccac ctagtaagat caatgcgtag agtatcagca   22200
tggaaccgcc gtattaaggg cgtgtgtgac gttggatctg catacttgtg caatcagag   22260
acgaagaagt caggctgcag ctcctggaga ttgacctcga actggcccac gctatgcgcc   22320
ccgtcgacca acgtcatgat gccttccttc tggcatacgc gcagcaagtc ttcgaacggc   22380
atcctaacag cagggatgct cactatcgtc tctagaattg ctaggcgcgg gcgtagaccg   22440
tcagccctga tttgggccat ggcagtctca aactgggaca caatcttttg cccgtcgtg   22500
gggagctcaa actccaccct acgtgtcttg aagggccgag tctcggccaa ggaagtgatg   22560
ccatggtcga tggcaccgta agtagttgat agagtcacca cgacgtcccg ttcctcaaat   22620
gcctggttgt aaaggacggt gaagatacca gtagtgacgt tggagacgag gacgcactcc   22680
gagacggcgg catgaactag atgagcgagg ccgatactgt gcctcctgca gcaccaagcc   22740
ttgggaaaac tcggagaaca agtcgggctg ggcctccagc agggaccagt aatctctgat   22800
ctgcttgctc accaccttgg gccatgaccc acaagatgct acgaccacgt cttgttagtt   22860
cagatacagt caacatggaa attgaaacgg gcacatcgtg tgacgggcaa ctgacaagaa   22920
ttgaggttgg tgtattccgg atccatgcag aaagcctcca gcataggctt gccgaatggg   22980
atacgcttgc tgttcactgt catcttgaca aggcgatgtc accgaacaag taaatgggaa   23040
tcagtgagag tagagatgcc agcagcactt ggtgaaaagg gacacgtcaa gttaaagcac   23100
acggctggca ttcttatgat ttacccaatg ggactaaaat caccccatcc acatcccgtg   23160
gttgattagt agctgagcag accacatgca ttgtgtgggc ggggtgataa tatgcaagga   23220
cacgtctatt cgcatctcat tcttttattt acatatgtcg tttgatcatt ggatgcgtct   23280
ggtcaagcgt gcatatgtat gcttgcctct ggaaaagttc atctttctga aagggcagtc   23340
agatatttaa taaacttcat tactccaacc catacccccc ttcgtcgaag ctctctaaat   23400
aacagtccaa cctacgagac aatcacggtg aagccctctg tttcacttaa tccatcatga   23460
ccgctgcttc ttcccctcac ccaggcgtct ctgcagagga catcgaattc taccaagcca   23520
acggatatct tcgcctgccc caagaggctc acggcctgtt cgacgacttg gcaaagttgc   23580
aggcatgggt ggcagaaatc tcccagtggg gcctggaaac ggggaaatgg cgacattact   23640
acgagacgac gaatggcaag catcttctct gggggacgga gaagctcatg gaataccacg   23700
cgcccatgcg agacctgatt gctggcgagg cacctctcac actgctcaag tcgctgacgg   23760
gcaaagacat ggtggtcttc aaggacgaga tagggtggaa actcccaggc gggaaggggg   23820
cggtccctca cctcgaccgg cccgcgtact ccatgtttgc cccgagttc atcgagatca    23880
tgatcgccgt cgatgcccat acggtcgaga atggttgttt acagtttgta ccaggctctc    23940
acaaggaggc agtcccgatt tcggccgacg gccgcattgc atcggcgtgg ctagagggca    24000
aggagttcat ccccatggtc ctcgatcccg gcgacgtctt gatcttcaac gagagcatgg    24060
cccatcggtt ggatcctaac aagacggacc aaagacgtgc agctgtcttt ggcacctacc    24120
actttgaccg gtcccagccc gacctgcggg acaaattcta cgcccaccgg ctcatccaca    24180
```

```
gcccccccaga aaacggtaag gcttttcctt ggccagatga tgtttgcatg tttggaggcc      24240
aatgctaaca tgatgcgtga ccaatctcac gtagcctggg ttgaaacagt ggaagcgcag      24300
acttgacaag aacgtacgt ataacgtagt ctagatagca cgcacaggaa gttagttacg       24360
aggtaggggg tcgaaatgga acttggcatt caccatgtca aatattgtct tcgctatagg      24420
caagcacatt tgcacagttg ttgcgtctta ttgttcgtgg ccggtgtaaa atcacacgcc      24480
cgtctttcaa tacctagagc acgtttgcac aatcccgtat ctcctgtcct tggcaacttt     24540
acattctgtt agatatagca gcctcacatc ttaggcatca ctcctataat accttccctc      24600
ttcgtggcta gttatactgc cttagcactt agggcaaaga ccctctttta ggcccttata      24660
tatagcctta ttaattaatt tttaatttt tttggggtta ttagttatag ccaatgcatc      24720
taatataaga aaaacataat tactagcgat acctagctag tataacaatt aacatataat      24780
taatattaac tatagtaata aataaaaccc tatataagaa taagctttaa gattataaat      24840 ataggggct ataaggttag attaaagttt ataataaact ttatagctat attagcataa       24900
gatatagtta tagtttataa ctatagttaa acttaaattt atttaagttt tacttatagt      24960
ataaattaat ataattcccc ctttctttat aactatattt attcttgtga gaacaaagga     25020
tagctaggta tgagacggtg tggaaagtga taatgatgta ttcagctatc taggctattc     25080
acacatgtgg cataacaagg ctataggtat aagggtaaag agggtcttta ctctaagtcc     25140
taaggtacta taatctatag taacctataa ccttaaataa ggaagttatt ataagtaata     25200
cctaagatat aaggctacta tatttaacac taccccctagt aaaatatcta gcctaaagat    25260
aaagctataa atataactta tttactaaga tacttacttt actaaagtat ttttatttaa     25320
tataaagtct tataccttta ttattt                                          25346
```

<210> SEQ ID NO 16
<211> LENGTH: 16397
<212> TYPE: DNA
<213> ORGANISM: Neotyphodium uncinatum

<400> SEQUENCE: 16

```
tataagcttt tattatagcc tatagtaatt ttataaagta aactagctag ttcttatacc        60
ttaagaatta caggaggtta cttatcttat aaatttatat aaaaagatat ctccttcgtt      120
ttaggcctag ttattactat ataattgaaa aatcactact gcatgtttac gtgttgcttg      180
acaagacctg tggatcgggg tccaattacc cctacaggtg tgtaagagga catctacatg      240
taaacacgca tctgtcaaaa attgaacacg catctgccgt tagtaatgca gcccgcatta      300
ttaatgcaga gaaactaacc catagtctct taatattaca cattataata ctataacaat      360
cgcttctttt tattccttta ctattatatt attccctaag atatagctat tgtatactat      420
tatagaagct atggttaatg ctatttagat tgttagacgc aagccacact agaaacaggt      480
aggtaggtcg tttatcctga ttaggactaa cggcagatgc gtgttcaatt tttgacagat      540
gcgtgtttag aggtccggcc taagatggac atgaccaacc ggctagatcc ctgtcattgg      600
ctttgcctgg ccctccgctc tcttgagaga caagatcgac ctggtggcta aatttgcta      660 ccaagacaga ttcgctgaat atctgcaagc aagcaagctg cattatcaaa acataaataa      720
cgaccataaa ttacacggag tcgaagaaag aaaggaccag aacaagttgg cgattttcca      780
acttggttac tcacccgaac cgtcactctg ttcatatcat cactcgcctc cagtgtcttg      840
cccaccttgt ttcaatattg tcgtcgagaa aaatgacagt agatacgatt acttcgactt      900
ctaacgggaa ccaagatgtc ccaaaggaat tccttccaat tgaattcgaa actcagcttc      960
```

-continued

```
ttcatcttgg gtaggttatc gcatctcata tgacggtcct ctattccaga actaatcagt    1020
ttgcgattca agccgattcc cggacatttt aggcagttgc gcagtgcctg tatacagttc    1080
ggcagtaaga tcaagccacc gcctcctcga aacctaccaa ctatgcacat gtactgaatt    1140
gttttccttt ttgcgcatct aataggcct ttgagttcaa cagcgttgcc cacggtgcgc    1200
gtcttctaaa cttgacgcag ttcggcaaca tctacagccg cttcaccaat gtttgtctct    1260
ttctccttct cccgcatgac tgcttttccc tgacgaggat acaagctaat aaaacacaac    1320
catccttcaa cagcccaccg tcaatgtatt gcaaaatcga ctggccgggc tggaaggagg    1380
cgtcgctgct tgtggcgtcg catccggctc tgcggcggta gtcgtgacgg taatggccct    1440
cacaggcgtt ggcgacaact tcgtctcatc ctttcacgtt catgctggca ctttccacca    1500
gttcgacagt ttagccaagc agatgggcat cgagtgccgc tttgtgaagt ctcgagaccc    1560
tgcagacttt gcggcggcca tcgacgacaa gaccaagttt gtctggcttg agaccatcag    1620
caaccctggc aacgtaatac tagaccttga ggcagtctcg acggtctgcc acaccaaggg    1680
cattcctttg attgttagta tcccaatgaa tactgtccat cccataggg gagttggggc    1740 taaaattagg ggggatgggg tttccatccg ggggatttta gtgcgataac acctttggct    1800
gtgccgggta cttttgtcgt cccatcgacc acggtgtcga tatcgtcgtt cactcggcca    1860
ccaagtggat cggcggccac ggcactacgg taggcggtat catcgtcgac ggcggtacct    1920
ttgactgggg ccagcacccg gatcgctttc cccagttcca tgatccacgg acgcgactct    1980
gggaacgctt ttcccgtcgg gcgtttgctg tccgctgcca gtttgagatc ctgcgcgata    2040
cggggagcac cctcagcgcc cctgcggccc agcagctgct ggtaggcctc gaatcgcttg    2100
ccgtgcgctc cgagcgccac gcgcagaatg cggccaagat tgccgactgg ctgcgcgagt    2160
atcccctcgt ggcctgggtc agctatgttg gtcacccgaa ccaccccgat caccagggag    2220
cgctcaagta cctcaagcga ggctttggct cggtcatctg cttcggtcta cgggggggtt    2280
tcgaagcagg tgccctgttc tgcgatgcgt tgaagatggt catcaccact accaagtgcg    2340
taattaaact agcccccttct tctcctgcga aacatcgtt ctgccattct aacctcgctt    2400
tgcagcctgg gggatgccaa gaccctaatc ctccatcccg cctcgactac tcatgagcac    2460
ttcagttccg agcatcgagc tgaggctggc gtcacagatg atatgattag gctgtctgtg    2520
ggtattgagc agatcaagga tatcaaggcc gacttcgagc aggcctttaa gcaagtgctt    2580
cggggtaaaa agagtcttcg taagccttgc atcggaaaga ttctcatgca ggatgagatc    2640
aatgaagact tatttggacc ttcggcttgt cgtacgtaaa tagggtcat tgcgaggcat    2700 ggtaagttttt cctaatagac ccgtaattca cggttgttac ttttttcatg tttgccatgc    2760
cgaatttatt ttcataatat tttttttttca agtgtgcaga actcgtagtc acttacaaag    2820
ctaaatgccg taatcaatct ttagtgcgcc atgtcctctt gaccagagct ttgcacttgt    2880
gtagtgtagt attttttgta gtatttttta tttaatttta tatctagctt ataattaaag    2940
gtattatcct aggaattacg taatcttatc tagcaaagtt ctaagaaaaa taccatatat    3000
aagggtaggt ctaagagtgg gttatcgccc tacaaattag aaaaactaca tttgtagtga    3060
atttttagcg gtaaagctag atatttgaaa aatgtgttac aaaataaaga tctttgatta    3120
tttaagcagt tttaccttat gcctagtaag gggtgttttg gaattatact actatattat    3180
taaataaaaa atatatacta ttatcttaaa tagtcaatta ttcacatatta aaacttatta    3240 tgcaaaaagg tgggagatttt ttgcatatct taccttaaat attattacta cttaatatta    3300
```

```
ggctttccac tgtttacaaa cacctaagct aggcggcgtg gcattaggca attacgagaga    3360
ctgtctcgct atagcacgga gtatatcaga atcatgtatc atacagatgc cgagccaaat    3420
gccgtccatg atcgaaacga agccaaagcg cagcacgcca tcaagatgcc gctgtaatct    3480
cggttgtcac ttggaaacac ttggaagcac tcgtgcataa tgcaagtcgc tctctcatac    3540
atggcctaca gagttcttga gggaccagaa cagacaagtc tgaacttttg gcaaggaagt    3600
agctggacaa ggtttgcaga cgctctgacc gatcatagac caatattgga ggctggagac    3660
tctgccatat cttcaatagg ccctgatgta gccttacttg tgtgtgtact gcagggatg     3720
tttataaata tgtgcgggtt cgattatctt gttcggtttt gtaaactcaa actcgccagc    3780
tctcagcctg tcagccactt gagtgaattg ttattgccat tgttttactt cagaacacgt    3840
atcttgcaca attttcagtc gcagcaatga cgacagtcgt acgagaagca tttgagaacc    3900
atgtcaagct ggtcgagagt cggaactcgc ccggccatgt gcttgcttct tctgaggcct    3960
ccttctttgt tgccgacttg aacgacgtcg ttcgtaagtg ggcggcgtgg aaggaagctc    4020
tcccagatgt caccccttt  tttggtacgt cttcaattcc ccccatttc atgtctcact     4080
aagctgggaa gtcccgtccg agggtccgaa tcaattgact tggaggcagc cgtgaaaagc    4140
agctatgatc gacggctgat ccagactctg gccacctgtg gagccggatt tgactgtgcc    4200
tcgacggagg agattgagtt gatcctgtcc ttgggcattg gggcagaacg aatcatcttc    4260
actcatccgt gcaagcccgt ctcctccctg gggctgtgcc gcaagcttgg gatcacgctc    4320
atcacttttg acaacgaatg tgagcttcgt aagctccacc atcactatcc cgaggctcag    4380
accgtgctcc gagtcttcgc cgacgatcca accaatgccg atcccttggg taccaagttt    4440
ggcgccgcgc gggacgactt tgatggactc gtccgtctgg ttaaggagtt gaacatgcag    4500
ctggccggcg ccagctttca tgcaggtgcg tctcgctctc ggtatcttgg ccggtaaaat    4560
gcatgcatac agctcgctaa cggcggcaat tccacaccct gttccactgt tccagccccc    4620
agcgtcgctg tcgatgcagc tgcatacgta cggggcatcc gggacgcagc cgaggtcttc    4680
gcgcgggccc gacaggtggg gctgaaccct acggtgctgg atatcggcgg cggctacacg    4740
gactcgacgt ttcaacagat tgcaggggcg gtcaggccgg cgattgccga gtgcttcaag    4800
tcggaagtgg gcgagggacg cctgcgcatc cttgcggagc cggggactct cttctcctgc    4860
agcccgttct atctagcagt caaggttgtc gcgcggaggg tgaacgccac tgcgtttggg    4920
catgagccag ccacgcgtct ctacatcaac gacggcatct acagcaactt catgatgcgt    4980
ttcatcgtca acatgacctt ctcgcccgcg gccgtcatcc gggagggtgt gtggcacgat    5040
caggcggatc atacgatgcg cggcgaggcg tgctctcttt ggggccggag ctgcgactcc    5100
aacgactgca tcaacaggga ttgccggctc ggtccggaag tgagggtcgg ggactggctt    5160
gtcttcaaag acatgggggg tgagcgtttc ccctttccc  cctgtggaga atagcataca    5220
tgtattagca taggagctaa ccatgcatgg tgtggcagcc tacacaacgg tatgcaacac    5280
cacgttcaat ggcttcacca gctccaatca cacaatctac ctggaacctg aacccaccc    5340
aagtcgacga agcccagtcg acctttgaac agttggccat cggcccacat acggtacgga    5400
gtacgtggtg ctgtaccgcg tcccgtccgc ggctgcatgg cgatggtgat agacgcgcta    5460
gactgatacc tacatgtaca tactccggta cggaagtact gtccttgtag tagtccgtac    5520
atgctttagt cacaacggat gacttggatc aattgatgca cactccctgg ttcgcttgtt    5580
tgacattcgg tttggcttcg tgcgcatcat gttacagcca ctccatgttt cctccagtcc    5640
ttttcgtatg ggccatgatt cattcaaccc gttatcatgc aagcaattat gtagacggcg    5700
```

-continued

```
acgccgagct cttgcaagta ccttgtacgg agtagagccc aatttcctg caccaagcta      5760 ggtgccgcgt ccccggaaaa gcggggcagg ggtccacccc gagaacggta aaaatgacga      5820
cacatggcgg aacccctct cttggcgaca atcacaacaa gacggacaag gtattacaac      5880
gacctgggtt tctgaccgac tggcagaagt gctcatgatt gaatactagg tagcagcaga      5940
ctgtacggac tagttcattg tttcggtgca aatcacttca ctgctataag cctcaggcct      6000
ccgtcccctc ctacatgacc gttgctgctg tcttgcgctc atactcaaga gcaactcggc      6060
gggccagcca ctgccctgcc gtcatcagat ccttccactc gagcgtgctc cacttccctg      6120
gcttctcgca gccaggcaga ggtttgatca tctcgtccag attcaagtgt ccgaagaaga      6180
cgagcgagta gcgctgcacc agctcgtcat cgccaccggg acttcctccg tacatgtacc      6240
ggctcggcgc cgtcacgcgg tggagggcgc tccgccatct gccgttggtc tgcttctcaa      6300
gcaggtcccc aacttgaaca atcatagccc ccttgatcgg aggcacaggt ctgtaaatgt      6360
cttcctcgta gtcgtgcagc tcaagccccc cgaccatgtc ctggaagagc atggtgaact      6420
ggcagtagtc cgtatgcgcg ttgagccggt tcgaggatcc gctggccagc tgtgaaacgg      6480
gctgccccag gaaatagttc caggttgaat gggtgctcat gtggcgcggc tcaaactttt      6540
ttccaatgta atccaaatcc tccatcccga ggatttcgca cacgaggcgc atgttctgga      6600
gagattgctt gtagcaggcc gcgaaccact tcttcaagaa gtcgagatag cccgggagat      6660
gctgctccac caagtttaga tctgggttgc ccggggggta cgttccgcaa gggtcctgca      6720
gctccatggc ctctttgagc tccgtcggca tctccttgcg gagcctctcg atctcgtcgg      6780
ggtcccagac gccctgcgag gagatggcct cacctgtgcc cgtccagccc tggaaatgct      6840
ttgatacgtc aggtgggatg tgaaccgagt tcttgaccgc cagaggcagg tcaaaaaact      6900
tcttgcactg catttcaaag gcacacggga tcaattagcg ctcctaactt gtatggggaa      6960
tgccagccca ttcttgagta accaggccag ctacttaccc agacgaatgc ttcctcgagc      7020
gtctcagtgc caatactgtg attaataaca tagacggctc cgtgatggct ccacgcctcg      7080
tcaagctgtc gcaagtattc cttacgctca ttcccgacac tggcatggat tgcctcaaag      7140
tccatcactg gcacattagc aggctcaaca ggcttgtttg ttaccgtcat ctttggagtt      7200
agacagataa aatcttgatg ctgaatttgg gattagcgtc tcggaaagag tgaagaattg      7260
tgatttgtga ggtggatcgt tgaataaagg ctttgggag atcatttata atagtgttca      7320
caggctgatt cgtcgcactg caatcctgca tgtatatgac acggtctcta ttattggagg      7380
gattctgatt aatgggatca taaatgcgca taccactgcg ttctctgaat gcatactgcg      7440
ttagtcctag aacaaaacaa gtacctttct atttaatccc ttgctaaata tactagctct      7500
ctttagtagt aaatataagt ggcttactat aatgcttata acctcttcta tagagacttc      7560
cctaaatgaa attcctttat ttttattatc gtaaaagcct tataatacaa tgcaatgcaa      7620
cgcaatataa cggaatgtaa caaggctctt tctaattact ctttattatt ttattcttta      7680
agatatagct attttatata taactataga aaatattatt aatattatta atacttagta      7740
agtaagggat tcatagtaaa tagatctagt aataattact caaggtttca aagtggtatg      7800
atcccattat attcactagg ctcctctcta gggacacgat acaaatcttt ttaggctaag      7860
tttgccattg ctatgagaag tggctgccaa gtacttcgta atttaagagc atcgcgtctg      7920
gcgaattcca cagacacgga acgtcagtaa caccaaaccc atccagccca cccacaaaat      7980
ctcaattgaa ctgtattttc taacgatgct tgatgaaagc ccgatgcgga agggtaattc      8040
```

```
tgtgagcaac gaccaaggca acccagagag caatgcatct gtttcaatcc accagcagaa    8100
tcagatcatc acctgtgcct ccccaggtcc agtctgcccc aatgccatag gcatcaagcg    8160
tgacattgtg gtcgtgagac tacggcccgt caaaagttgt ccagactatc gcttctttcg    8220
ccgagtcttt gagacactag agaaatggca gctgcaagtc gacatgttct caaccagtct    8280
ggggcgaata accttggcgc tgggggccgc agcgctgcaa ccggcattg gtgactcatg     8340 cagtgccaga aatgacatga tgagccggga tctcatgcac ggcatgcaga agctgctccc    8400
ggacgatcac atattagagc tctttcctca catggccatc atctcggtcg ttggacaccc    8460
gagccgacga attgctggcc acatcttcgc caccatggat gccaatgata ttctcacggt    8520
catgatttcg cacggtatgg cctcaatcct ttcccgtttc catagaaggt catcgtccca    8580
ctcttctgac cagcatgttc agacgccgcc aggctcggta tagcctgtgt catctcggag    8640
cagcacactg ctaaagcttt gggcgtcttc gagcaatgct tattccggta ctccttgaca    8700
cattgaacag ttatctcagt ctcttcatca aaacgcttct cattgcagaa tcatattaga    8760
tgcacaagac actccttgtg ggctatggtt ttttggccg cgatagacag ctaaaactaa     8820
attctcattg tagctacaag cagctttatc acttcccgtg atactgactt ttctttggca    8880
gctgaccgac cactctagtg acatgacaac gacgttcaag cctccttcgg atctagtcct    8940
tctgaagact cacttccatc gagtcccaac tcctggagaa gactttcgcg caccatctcc    9000
atgacggaag ccagaaagtc ttccgtatag taagcatcat tgtagtacaa gtacagccgc    9060
atagtgccgc ggaaggtaaa tatctggaac tcgatggttg gatcagtcgt tgcattgacg    9120
agggctacgt cttcgatctc acaaacagga gcttgtgccc cttttgccc gtacgcacgc     9180 gctaggtatc tctccaacac gccgaggctg ctgaggttcg gtacccggaa gggcggacag    9240
ccggcaacgg gcaaggagcc aaggaaagcg gcctcctggc tgtcatacag cggcagcaac    9300
tcgagaaaac tcacagggtc gcctgccgag tctgagggca gcgccgacag atctcgcgag    9360
taaacagcac ccagacgttg cgtgaggtcc tcgaagccac ccgtgagaca gaacggcacg    9420
acaaagatac agaggctaag tgcgtagtcc ggaaccaccc atttgggtc cagaagtgga     9480 cgcaggttcg cgacgagggg aatgagcatg ttggcgcgct ccggtgtgct gctgttgagg    9540
ggaatgaggc cccagacgcg gacaatactc gcgtgcacgg cggccgagac gctcacgccc    9600
agctcttgca acccgccacg attgcctcaa gcgtcggctc gtcgaacaag gtcaccatgt    9660
gttgggtgtt ggcaggcgcg gcgtcctcgg accctcacg cacagggaga gacaagctgt      9720
acaaaccatg atgccaatgc cgcatcagct catcgacggc acaccccacc cggtgtgaga    9780
cgggtgtctc ctgcggcggg aaccccagaa tatagtcgat gccggcgggg agggacggtt    9840
gtttgacgtc ggtagtgtag caatctaggt tggcgtcgag gccagacgg aagactgact      9900 caagaccgag catgaaggtg tttgtcgcct tgtatagtcc cacagcgtca atcggaggt      9960 gagtgctgcg aataaccaag gtcgacgacg gaggaaacca gtaggccatt gccgttggac    10020
gaggtcgaaa gatcattccg gcatcgtcca cgtccctgaa aacggcctgg ctcccttggt    10080
ttacgtggaa acttagccgc agccactcct caggatccat tggggggaacc gtaaccaggt   10140 accgccctgt ctcatctcgc tctgaatagg gcggatagat tgcgcctatg agcggctgga   10200
cgtatcgaaa aacaagccaa gcgcggcgga ggtaggggat ggggtcatca atgtcttggg    10260
gcagtcgtaa tttgagcttg taggtgaggc cctcggcttc acgaccagga ggcgtgttgg    10320
cgcgttggat acgggcaagc agccagttct ccaccaagtc gaggggcgt gtgagagtgc     10380 cgtcttctga tgtggtccat ccgagagcga caatggcatg attccctgcg ctgaccatgg    10440
```

```
ctgctctgcc tgttaagaac ggcggggata gtctgggaga gtaaagcagt gagggcgatt    10500
ggatatcgac gacgaaaacg aaggaagttt ccaactagca ccataggcaa gccacctatt    10560
tgggcgactt taccgaatca ctactacatc ttgtgatagt ccgtacttat ggtatttcg    10620 acagcactgg tgtgatactg catgatgtaa ccgcaccaag gtgccaaatg acgtgtctca    10680
tacctgcctt atgcacgcta gaagcggtga catctgtgac taggccgatg ggtcaataaa    10740
tgcgcattgt accgcgttgg tcctaatccg ggttaatagt ccacacactt aactttagta    10800
tagcttatac ctataatatg aaaagctata acattgtta aagctattat aattactatt    10860
atactgtatt aaattaagta attaactctt attatttagt gctttaataa tgattactaa    10920
attaatttat tataaatccc ttactaactt actaaatact aaaagtattg attatatttt    10980
cttgagttat attaatagct atatcttaaa gattaatata acaaagggca ttcaaaaaga    11040
gccttattac ataatgttac attgcattgc gttttatttg tggtaatcta ggctctgcct    11100
agacctagta atatagttgt taatgtatgc gcatttcgta accctaggct aatcgtacac    11160
acatgtccga tgttaaggac attcacagtc aaggaattcg gatatcgacc ttgccagcag    11220
cgtccgtgcc gcgcggggag tcttgctctc tctttgggtc tgtccaatgt ccggcgacct    11280
gatcatatga tcataatcac aaacgtagca cccataacct ggggtcaata cataagtcag    11340
cccatgtgtt ctcaaaggag ttttctagtg tccccatcgc cggggacttg atctctcgta    11400
gcacacgcac catcccaccc attgccactg acggctcata cagaacttaa tggatctgac    11460
ccaattcaac acagctggca tcgtttggct gacggtcgct gccatcgcca tctcctatat    11520
cctgcagtcg agctttctct cttggtacag gctacgccac atccccggcc cttttcctggc   11580 ctcgatctca agtctttgga atgttctaaa catcgtgact gggcgtacgt cgccggtgct    11640
cgagaaactg ccaggaaggt acggcccgct ggtgcgaacc ggccccaact acgttctcac    11700
agacgatgcc gaaattttgc gtcacgtcaa tggcgttcgc agcacatacc cccgtaatgg    11760
gtgtaagtct gtccatatca cacgtctttt gaaatgtagg gagactcaga gactcactta    11820
tactgtggct tccagggtat gaaggcttca gggtcgatga atacgaccat atggggtccc    11880
atatcgacac gtcggtacac gacgccatca aaagcaaggt gattggtggg tacaacggca    11940
aggatgggat agacctcgag ggggccatcg gatcgcaggt caagaccctg gtcagtgaga    12000
tccggcgtac acgcggctca aggccgagat caaggccgcg gtggatgccg gcgaggtggt    12060
cgaggtcatc accatagccc aggcccagag gctgccgtat ctgcaggctg tcgtgctcga    12120
gggcttccgc atgcgcccgg ccgtcgtgta cgggcacttc aagtcggtgc cggccggcgg    12180
cgatacgctg ccgaatggtg tacgcctgcc tgccggcacc gccatcgccc caactacat    12240 agcactgacc cggcgcgccg acgtctacgg cgctgatgtc gatttgtttc ggcccgagcg    12300
tttcctcgac gccgagccgg ccaagcgcct cgagatggag cgcgccatgg acctgaattt    12360
cgggcttggc cgctggcagt gcgctggcag gaacattgct ctcatggaga tgaataaggt    12420
tttattacga ggttggtgga tgtgcatctc cgctctttgc ttttgttctt ttcctgctat    12480
tgccctcgcc ctcctttgct atcctgacgc gggagaggta tgggacgaga tgagagactg    12540
attcaatgcg cagttattac gccacttcga cctccagatc gtgtatccgg gcaaagcatg    12600
ggatgaattc acgtaaggcc ttctgaaccc ttttcaccct ttcgcgcata ggcgtctcgg    12660
gtggcgcgag cagcgtgcca tggatattgg agtgctaacc aggttacctc ttacctctgc    12720
aggggcgtgg tatattcgca gcataacatg tgggtacaaa tcacggagag ctcgtaagta    12780
```

```
tagtggacgg gaatacacat ggcagtggtg gccatgaacg tcgatggcca cgtacgaggc    12840
cggtaccaat ggttggggga ggacacggct gagacggctg gagagaacca tggagatggg    12900
gtaaggaatt atagcaatcg aaataacgag cgtgtttgtg cgcgccgggc tttgcctcac    12960
actgcctacc taaacaagtc cccaagtgat gaataaaatt tggcctcggt gccttctaat    13020
ttgctctgag ccaccaatga aaatcaact  tggttagaaa acctcctcac caaaaccata    13080
ttactagcgt gataagcaac acctgcaaat gcgtaggcag cttgtcatct aaaaggccga    13140
caaccgcagc atcttgggct gaaaacttgt tacccaagca tcttgcattt ttggttggct    13200
cgaatttagt cgtgccacct atatgagtcc gaaatctctt gtcccatctc cctgctgagt    13260
atctcttcgc atattacctt gagagcattg ccggccatct caaaatcact gacctccaag    13320
tatacttgcg cacagagtct agcccatatc catccgcggc aatcggcgat gggtatccag    13380
gtcttgtatc tatccgccag agcctttgtc aagtaacgaa ctgccgggcc gacctctttc    13440
tccgtcagag cgccgcccgg cacatgagct ggggcagtgg acgggcccgt ggcaatggcc    13500
aagggaagtc gcactgtcac gatgccgcag tctctcatct ggccatccgc cccggccccg    13560
agaccaggct cctccaagac ctctgtctga agtatctcgg cgaccttgtc accaccctct    13620
ttagcgagcc acttgatgta ctcgtaaatt gccgcctcgc caccacagac gtctcgcctg    13680
aagcggaggg cggtcgggat gcacagatgg ggcatgttat cgctcgtggc tgtgtaggca    13740
aacagtgtct cgaatgaaga cgctgttccg tttgcactga ccatctgcga ccatagggga    13800
agttgagagt tgccattctt gggaataaat ccgaaagagg tcgggatggc ggagcgcatc    13860
atgtgctggt tgcgctcggc aacgtataag aaagcacaag gtcgaggaac aaatagccac    13920
ctagtaaagt gaatgcgcag aggatcagca tggcaccacc gtatcaaggg cgtggagaga    13980
cgttggatcc gcatacttgt ggcaatcaga gacgaagaag tcagggtgca gctcctggag    14040
attgacctca aactggccca cgctgtgcgc cccgtcgacc aatgtcatga tgcattcctt    14100
ctggcatacg cgcagcaagt cctcaaacgg catcctaaca gcaggatgc  tcactatcgt    14160 ctctagaatt gctaggcgcg ggcgtagacc cttagccctg atttgagcta ttgtagtctc    14220
aaactgagac acaatctttt cgccagtcgt ggggagctca aactctaccc tacgtgtttt    14280
gaaggatcga gtctcggcca aggaagttat gccatggtcg atggcaccgt aagtagttga    14340
tagagtcacc acaacgtctc gttcctcaaa ttcctggttg taaaggacgg tgaagatgcc    14400
agtagtgacg ttggagacga ggacgcactc cgagacggcg gcgtgaacga gacgagcaag    14460
gccgagacgt gcctcctgca gcaccaagcc ttggtaaaac tcgagaaaca agtcgggctg    14520
ggcctccagc agggaccagt aatctctgat ctgcttgctc accaccttgg gccatgaccc    14580
acaagatgct acgaccacgt cttgttagtt cagatacatt tcacatggaa actgaaacgg    14640
gcacatcgtg taatgagcaa ctgacaagaa ttgaggttgg tgtattccgg atccatgcag    14700
aaagcctcca gcataggctt gccaaatggg atacgcttgc tattcactgt catcttgaca    14760
aggcgatgtc accgaacagg taaatgggaa tcagtgagag tggagatgcc agcagcactt    14820
ggtgaaaagg aacacgtcaa gttatagcac acggctggca ttcttatgat ttacctaatg    14880
ggacgaaaat caccccatcc acatcccgtg gttggttagt agctgagcag accacatgca    14940
tgtgtgggcg gggtgataat atgccaagga cacgtaaatt ggcatctcat tcttttattt    15000
acatgtgtcg tttgatcatt ggatgcttct ggtcaaccat gcatatgtat gcttgcctct    15060 gaaaagtgc  aactttctga aagggcagcc agatatttaa taaacttcac aactccagcc    15120 cataccccc  tttcgtcgaa gctgtctaaa gaacagtcca acctacgaga caatcacggt    15180
```

```
gaagccctct gtttcctgta atccatcatg accgctgctt cttcccctca cccaggcgtc    15240
tctgcagagg acatcgaatt ctaccaagcc aacggatatc ttcgcctgcc ccaagaggct    15300
cacggtctgt tcgacgactt ggcaaagctg caggtatggg tggcagaaat ctcccagtgg    15360
ggcctggaaa cgggaaaatg gcgacattat tacgagacaa cgaatggcaa gcatcttctc    15420
tgggggacgg agaaactaat ggaataccac gcgcccatgc aagacttgat ttctggcgag    15480
gcacctctcg cactgctcaa gtcgctgacg ggcaaagaca tggtggtctt caaggacgag    15540
ataggtggga aactcccagg cgggaagggg gcggttcctc acctcgaccg gcccgcgtac    15600
tccatgtttg cccccgagtt catcgagatc atgatcgccg tagatgccca tacggtcgag    15660
aatggttgtt tgcagtttgt gccaggctct cacaaggaag cagccccgat ctcggccgac    15720
ggccgcattg catcggcgtg gctagagggc aaggagttca tccccatggt cctcgacccg    15780
ggcgacgtct tgatcttcaa cgagagcatg gcccatcggt tggagcctaa caagacggac    15840
caaagacgtg cagccgtctt tggcacctac cactttgacc tgtcccagcc cgacctgcgg    15900
gataaattct acgcccaccg gctcatccac agccctccgg aaaacggtaa ggcttttcca    15960
tgaaaagatg atgtttgcat gtttggagac caatgctaac atgatacgtg accaatctta    16020
cgtagcctgg gttgaaaaag tgggagcgca gacttgacaa gaacaatacg cataaagtag    16080
acagaagaag ggatttggct aggaggtagg gggtcgaaat ggaacttggc attcatcacg    16140
ttgcgtctta ttgttcgtgg cgggtgtaaa atcacacgcc tgtctttcaa tacctagagt    16200
acgtttacac aatcccgtat gtcctgtcct tggcagcatt acaacccaga agccgacata    16260
ggacgccaca tttaatgggt cacttaatgc acataccgcg gaagtcctaa tcattaacag    16320
tccatacgtg tagcttgcgt atattgattt ttactataac taatatgccg atatatataa    16380
tattaccagc ccgggcc                                                   16397
```

<210> SEQ ID NO 17
<211> LENGTH: 7478
<212> TYPE: DNA
<213> ORGANISM: Neotyphodium uncinatum

<400> SEQUENCE: 17

```
gacgaaggca gtcattcaca gcatggaagc gccggggatc ttaacaggaa tttggacgat      60
aatggctctg aagaaagtgc cacgatatct tattcaaacg cggcttggat gctcccacag     120
gctcacaatg agacttttcc agtcctctta caagcattaa tgcggacgct cctgcttctc     180
tgtcaatgta cgccttggga cagtggacct ctcgcctcca cgaggaagcc ataccacgtc     240
gacctggtaa agcagaagca aactatccgt catttgctgc accgcaggag acggattgtt     300
cttccaaaat gcaagatttg gggcaagcta gcacatgcaa gtcatgctcg actttacgtg     360
gcagccctcg ttgaagcatt atcattgctt aaacatcttt tgggcgagga tatgcatggc     420
acgagatatg agcccgtgga agacattttc aaccctggtt acggtcttca aacccgatct     480
agagccgaca cgaaacagtt ccggagagtc atcaaacaca gagaccagca gcggcgaagg     540
gggcgaacgg tcgatcatgc aagttgaagt cgcgaatcta tctggtcagc tccgtcagat     600
atcgcagcta aagaaggcc ttctacgagc atggaggagg gaaaacaaat cagaaggttg     660
gattgcttcc aagcttaata agaaaaaatc ggctaactcc gatctccgtc cacggaagaa     720
gtaaatatcc ttaaccaggg caaaatttac cacggaaaaa gatgatctta ttaaattatg     780
aaaggaggac gagcaactta catggacgca aattcaggag cggcatggca accagttcca     840
```

```
cacgcgatcc aaggagtcat tccaggtgcg ctaatgtaca aggctgaaga gccgtaaaaa    900
aaaatgtgac ctacggcagt tgatgtggtg aacaaaattg gatatttgga aagaaatgtt    960
gtcacgtcgc acgccctatg gaaggtattg cagtggact tggatcttga tttaagctat    1020 ttagaggga atttcgtcaa tacttataga ggtctctgaa gttgttgctt tcctgatatt    1080
gccatctgta acttggttga tacagttgtt gttggagccc cctgttttca aagaattggg    1140
ctcccgttga catatttgct cgtggtcact tacgcctgtt ataactatgc gccagagtac    1200
cttggttatt ggactgttca cggatgacta gctgtaatcc atgtgatgca gtcggcactt    1260
ccgatttatt caatcatgtt tggtgcttgg tgctgcactt gaacacgacg taatgaatgc    1320
aatgggcaca caactgccac atttctctgc ttctgtgcct cgattgcgtc atagaatctc    1380
cagcctccat ctgaagcctc atccgcgcca acctcggaca agccaaagtc cttgtagatt    1440
attatagcat aaagactaag cagaccccaa acccaaaccc cgaattttgt cccctcctc     1500 ttcatgtaca tctacaagct ttacccactc attgctcttg ttcttgttac gctggagatt    1560
gtccaatttc cctgcgaact tgccaggagg tcgattcaag tcatcaacaa cctccgagtc    1620
cagaaggata aacgtattgt gccgcggtgc atcccgaagc tcgggtatcg cctcgaggca    1680
ggcggtcatt ttggcgtctc atgtcgtgga tagggcgtc gcggagctcc gagttgtcaa     1740
tgagggtgtc atgttatgaa accgcctcat cagctcggtt tacttggtcg gtcggcgtcg    1800
tggtgcggct gctgcccagg gtacccagcg gcgactcgtt aaaaaacaga aagctgaccg    1860
tcatttatag atcatctcat ggtcacgagc ccggccatgg ctggatatct cgcaagcagc    1920
tggacagatt gagaacaaac catcactttc aacttcctcg ctacaacaga attgaagttt    1980
gcggcgtagc ttgttgcagt cttcgtattg ggccattgct gctcctatcc ctgacttgat    2040
cgccaatagt accttcaagt tctccgtata cgaaatttcg tcatgacgtc aggctaatc    2100 cccgattatg cggtcaaggc tctccatggt tgttgatgac aacgcgtcgc acaaccctg    2160 aaaaatagca cacttaccaa ctaactctac tacaaaggta catttctcaa tagactgggt    2220
tagtagggca tacaaactga attattatct gtcaatagtg cctaagggg gagcggcaca    2280 gcgtggccac tcatgggatc aggtggcggg aaccttgcag tagatcccgt agctcgagag    2340
agctcgagag aagcttccgc cgaaaggcta ggacgggcct aggatgctaa ttctgggtaa    2400 attttttagga tcagactgag acttgaagat ctagactaga tcattctgat aactgcaacc    2460
cagggatgca ggagaggagg ggaaacaaca tctgtcggta attggcgctt cagatagaag    2520
ccgtcaacgg gtccatacaa tgcccccccc ccccccctga attatttttt gtcaaatcta    2580
aatgccctag tcttttgttc ctctctaata gctgcaatta gctgtacgtc cgtacggagt    2640
aagtattgct attattatta gtaagctaca aggaaaattc acggggtgtt aagtgccgct    2700
taaagatagg gagggggtgt attactagtg ccacacaaag gtggggtggg tgggcgtgg     2760 tctgtgtctg ttagtgttgc acccacaagg gcataattga tccctgccgc acgatagtct    2820
cgctactcaa ctagctgaga caagagtcca cccctagcta gtcatttcc aagacctctg     2880 taacttcata gtatgtttca gcactgtaca agtaccccac cgatggtaga ggtacttagg    2940
tatttaagcc gtagtctgca ccctcttaca gggtcggaca actcaataga ggtggtcaca    3000
ttgaacccta gcttcgcggt ccaacagtta ggacgcaggg gcgtaccgca attattaaat    3060
gcgtatgtac atgtatatgt accgcgttat tatatgtctg tggatctaga ataccggtcg    3120
acctgtcatg gtctagccct aagggctaat cgcgggtgcc tgcgccacca tgtgggtgat    3180
gtgcccaatc ccctgttacg ccataggcaa cgacaaaaga atacgtattg tacaagtcat    3240
```

```
cattgacttg tgcaattgac acctatattg ctaggcctag gcaaagccta ggctatcaca    3300
ccacccacct attttaatgt ggcttatgtt tactaattat tattaataaa atcaatagta    3360
tcttttatag ttatagagaa tagctatatg ctagggatta atataataaa gggtattttta   3420
aaagagccct ataatagtta tattatatta tgttataagg cctttttgata ataaaaatga   3480
aggaactata tagaagaaat tattgattga ttttttatatt tttttttgggg tcattagtta  3540
tgactagtgt atctaatttta taagtaatat gacaattact agcaatacct agttagttta  3600
ataattgaca tataaataat cacgactata gtaatagata aaacctgtaa ttcctaggaa   3660
taagctttaa ggtcacaaat acaggggggct gtaaggtcag agcaaagttt gcgataaact  3720
ttgtggtaaa agagattata agcattaaca tggcttccta tatttgctgc caagtacttc   3780
ttctagattt agactaacgt ggtatgcgca tttagtggtc ctaggacgta tgggccggac   3840
tgttgtaggc tctccgtcct agcctagcgt atctatgtat tggtctggca acaggcttac   3900
gggggctagc caagatgtag atttgaacaa gatgctatca aactgctatt gtgtctgccg   3960
agaaggttac tggcagatga caccgacgga acgatgccc attttcttct ggcatagaaa    4020
ctgagacgta ttggtgtttg tcaatactag agtcttatca gtggaacatg aaaagcgtg    4080
gggacaaaat ctgcctagtg gtcatccaaa aaaacccaat cgctacttgc gtctgaacct   4140
gaacagtgta tcgattcgat atacgacaga aagtggcttc acagaagagc cgtctcctct   4200
acataccatg cttgaaaccc ctccaggttg ttggccagac agttttccag ctcccgacga   4260
tacagaatca acccccaaac cctgaccggt ttgttagagc agtccacagt acaaagcgac   4320
aagagccttt gtgcaaccta ccaagttttc tcttccttgt tagcctcagc tgttttcttg   4380
cttttgcgtg catgtgtatg gtagagtgtc ttgtcccaaa gtaggctcat cttcttctcc   4440
cactggcagt gggacttgga agtcgcctcg agttgacaaa tgcccgcctg ttggcacttt   4500
gagatgattt cgcacaacca ctctacctga acagtgatga ccgcggggga gttgaccaga   4560
agtgtaggac actggggtcc atagaggaaa acatgttag ggaatgaatg gatggccatt    4620
ccagatgcg actcgacacc atcggaccag gcatcttcta aacggatgcc attccggcct    4680
ctgatatgaa gactcctgag cccgcttgcc tcgtcaccaa acccggtggc aaaaatgatc   4740
gcttcgcatt caactgtctg cccatgaacg cgaatacttg tctctgtaat caactcgatt   4800
tgctggttgc tgatgtcaat aatcttcaca tgtggttggt ccatgatctc gtaaagatcc   4860
tcttccaaac agggtcgctt gatgccaaag gcaaaagatg gaatctgagg caccaggagc   4920
tcccgtttgg tcacatcgcc gattctagct cgtgtccgcc gagcccagaa atcatacgca   4980
tcccggttgg cttggatgtt ctggcacaga tcccggaacc cagccatcca gaaagcccag   5040
cctcccgcca gatagcgttg ttgataaaaa tggtttcgct cctctattgg gacatccaac   5100
gtgtcctggt cacggggcac gtagccgaaa ccgttcgaag tctgcagtcc aagtcgtagg   5160
gcttctctgt ggtcgtcggg tctcatgcaa agtgccgttg ccgtctggtt cgggctgccg   5220
tacttgcgta gagtgaggca tggagactgc tggaatatcg tcatggcctt ggctatctta   5280
cccacagatt ggatgatctg aactccgctt ggccccgttc caatgacagc cactctctta   5340
ccgcgcatac tgcacagcgtc atgaggccat tttgcggtgt ggtagatggc accgcggaat   5400
cgagacattc ctggaatcct agggatattg agaaccgacg aaaaccctac agctggaatg    5460
aaccatcgcg cctcggctct tctgccatct tctaaagtga cggtccatct ctgggtagtt   5520
tctgagtacc tcgccgcgga aaccgaaaca ccaaactcaa aactagcaga gatttcccat   5580
```

-continued

```
cgcttgtcca cgtggtcaaa atatctgagc atctctgcac gggtgggaaa ttgctctccc   5640
cattcccaat cttggagaag ctctgcatca tagaactggt agaagggaaa taggctgtcg   5700
actgctgctc ccggataagc gttctcgcgc cagacacctc caagacgttc ctggcgctcg   5760
aacccttgga ctcgaaatcc gagcttttcg cagtctttag tcatagttca gtcctacctc   5820
tctactctat tcgtgtcttg gatggcaacg tagactcacc tgtagacagc gagaatacct   5880
gaaaaaccag cgccaacgac gattgcgtcc aaattggtca atgtcatctt agtgaaatga   5940
agaagaatta aataactata tgcagaatag aaccaaattt tgttgtatca gaaatgtcat   6000
caaaggctaa cagctccggg gagagaaaag cttgatcgag gttgaaattt actgaggtgc   6060
gtaagggact gatactaaga cggtcgatta tctgtgtgag aatggtcaga atgggtagct   6120
gcgcaattgg atagactagt ttgggagggg gagtatagtc gtacacatgg attcgcaaat   6180
gggaatgaag cgttaagtct gttgtgatat aataaggtca ctaaatgcgc ataacgcgtt   6240
agtcctaatc cgggttaacg gtccatacac cttgtgccta tatgtgtaat atttaaaggt   6300
atcaatacta ttaaagctat tataattatg actatactag tattaagtaa ttaactctct   6360
attatgtacg ctttaaataa ttgctactaa ataaatttaa ccgctataaa tcaatcactt   6420
gcttaataag tattaatagt attaattata tcttgtatag ttatataaat agctttatct   6480
taaagaatga cacaataaag ggcatgtaaa aagagcctaa ttacattata ttgcgttgtg   6540
ttgtgttgcg ttatattata ttatgaggct ttttacaata agcattatag tcagtgcatt   6600
ttatactagc tctctaatat atttagcaag gggcttagta tactagtact ttctttttag   6660
gaataacgcg gtatgcgcat ttactgacct agtacaatac acccccctgaa ttattttaca   6720
aatctacata acaggggtaa ttaagctaat tagatattag ctaggaaata aaggagatag   6780
ggggtagtac attatactac tagttatcta tatagaaata gatatacttt ttcgtggcgc   6840
tatatacctt gtatatttcc ctcattgctc tctaaaacaa aacagaggtt atattacata   6900
tatagctaat catagctatt agagagagac gaataactag ggcatgtaga tttgtaaaat   6960
aattcagggg gtgtattgta taatagggca taggagaggg gtgagtgggg cgttcactcc   7020
gtgtcatgtc acttctcaca caaggagggg aagcgttgct attcggagct gtgttttctt   7080
gcttaccaga gctatgccta ccacgtaata aggccacatc ccacatctca cgccccgcca   7140
ctaaattatt tgtatagcac tccctggcaa taaaaaatag ttagaattac agtacacccc   7200
ctgaattatt ttacagatct tcataacagg gttgattgcg tgaattaagt gctagcaagg   7260
aaataaggga gatagaggct aggattagga agtacctaga ttcctttata ctatatttaa   7320
aatttttcat atcttctagt agtactacat accctacata ttttccttat agctctctat   7380
agtaatataa gtgttatagt gcacttatag ctaactaaag ctattagaga gaaacgaaaa   7440
aactagtgca tgtagattga aaaaggctga tagaccag                           7478
```